US008718347B2

(12) United States Patent
Ichihara et al.

(10) Patent No.: US 8,718,347 B2
(45) Date of Patent: May 6, 2014

(54) IMAGE DISPLAY APPARATUS AND X-RAY DIAGNOSIS APPARATUS

(75) Inventors: Takashi Ichihara, Nagoya (JP); Takuya Sakaguchi, Takanezawa-machi (JP); Kazumasa Arakita, Nasushiobara (JP); Yoshihiro Ikeda, Sakura (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 879 days.

(21) Appl. No.: 12/769,106

(22) Filed: Apr. 28, 2010

(65) Prior Publication Data

US 2010/0272344 A1 Oct. 28, 2010

(30) Foreign Application Priority Data

Apr. 28, 2009 (JP) .................................. 2009-109347
Mar. 16, 2010 (JP) .................................. 2010-059785

(51) Int. Cl.
*G06K 9/00* (2006.01)
*A61B 5/05* (2006.01)
*A61B 6/00* (2006.01)

(52) U.S. Cl.
USPC ................. 382/132; 378/4; 378/20; 382/128; 382/131; 600/407; 600/425; 600/431

(58) Field of Classification Search
USPC ......... 382/128, 132, 131; 378/4–20; 600/407, 600/425, 431
See application file for complete search history.

(56) References Cited

U.S. PATENT DOCUMENTS

| 4,672,651 | A | * | 6/1987 | Horiba et al. ............... 378/62 |
| 6,047,080 | A | | 4/2000 | Chen et al. |
| 6,137,858 | A | * | 10/2000 | Horiuchi ..................... 378/19 |
| 6,501,848 | B1 | | 12/2002 | Carroll et al. |
| 6,628,743 | B1 | * | 9/2003 | Drummond et al. .......... 378/8 |
| 7,496,175 | B2 | | 2/2009 | Sakaguchi et al. |
| 2004/0249270 | A1 | * | 12/2004 | Kondo et al. ................ 600/425 |
| 2005/0163357 | A1 | * | 7/2005 | Makram-Ebeid et al. .... 382/128 |
| 2005/0277830 | A1 | * | 12/2005 | Ichihara ....................... 600/425 |
| 2006/0241402 | A1 | * | 10/2006 | Ichihara et al. ............... 600/425 |
| 2007/0104317 | A1 | * | 5/2007 | Ohishi ....................... 378/98.12 |
| 2007/0123777 | A1 | * | 5/2007 | Watanabe et al. ............ 600/437 |
| 2008/0107233 | A1 | * | 5/2008 | Sakaguchi et al. ............. 378/91 |

FOREIGN PATENT DOCUMENTS

JP 2008-136800 6/2008

* cited by examiner

*Primary Examiner* — Joy Chng
(74) *Attorney, Agent, or Firm* — Oblon, Spivak, McClelland, Maier & Neustadt, L.L.P.

(57) ABSTRACT

An X-ray perfusion-image creating unit creates an X-ray perfusion image indicating blood flow dynamics in a certain organ from an X-ray projection image of a subject given with a contrast agent. An image correction unit extracts thickness information indicating the thickness of a myocardium from a three-dimensional image taken by an X-ray Computed Tomography (CT) apparatus. Moreover, the image correction unit creates a corrected perfusion image in which the thickness of the myocardium in the X-ray perfusion image is corrected, based on the thickness information. A display unit then displays the corrected perfusion image.

30 Claims, 14 Drawing Sheets

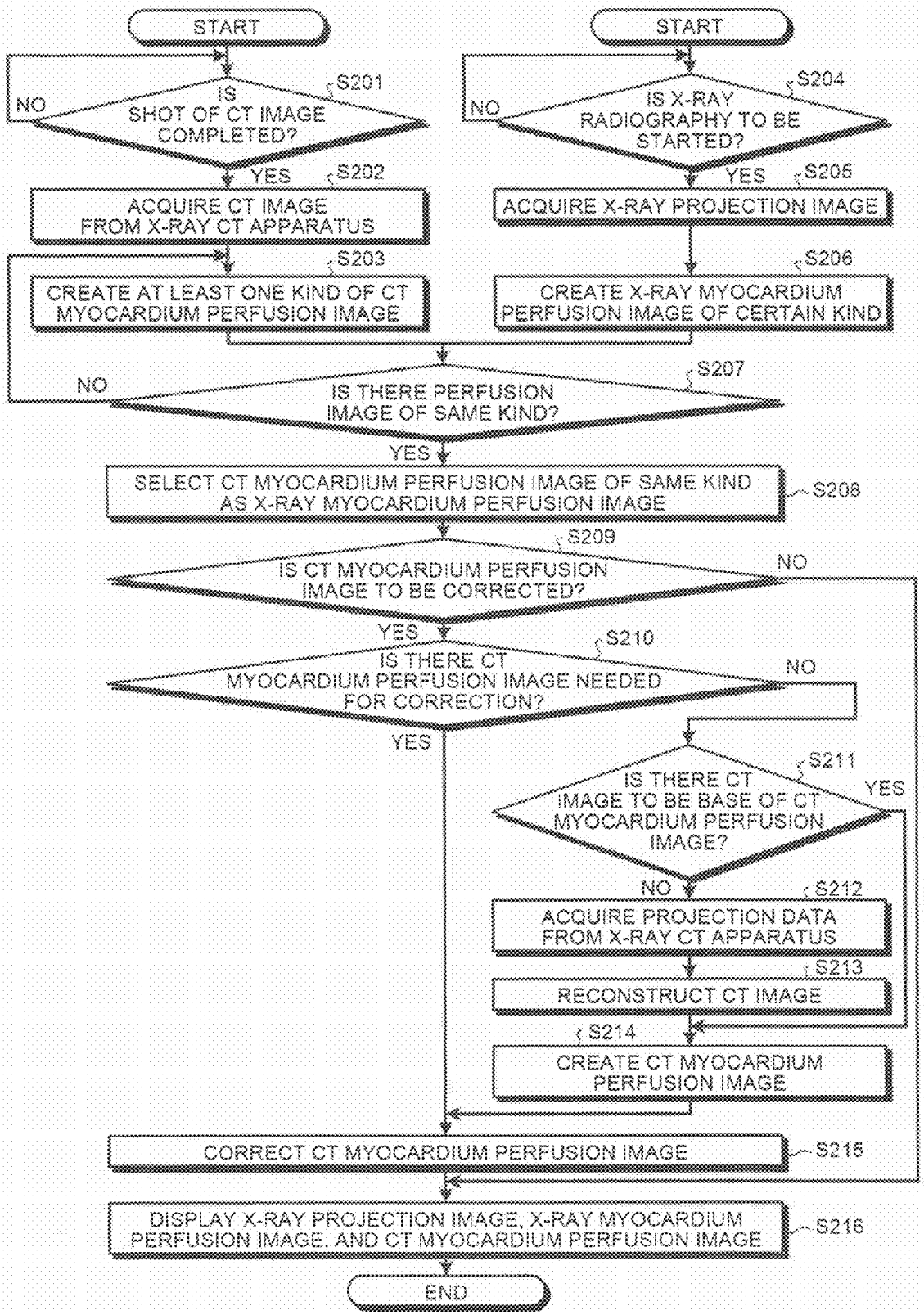

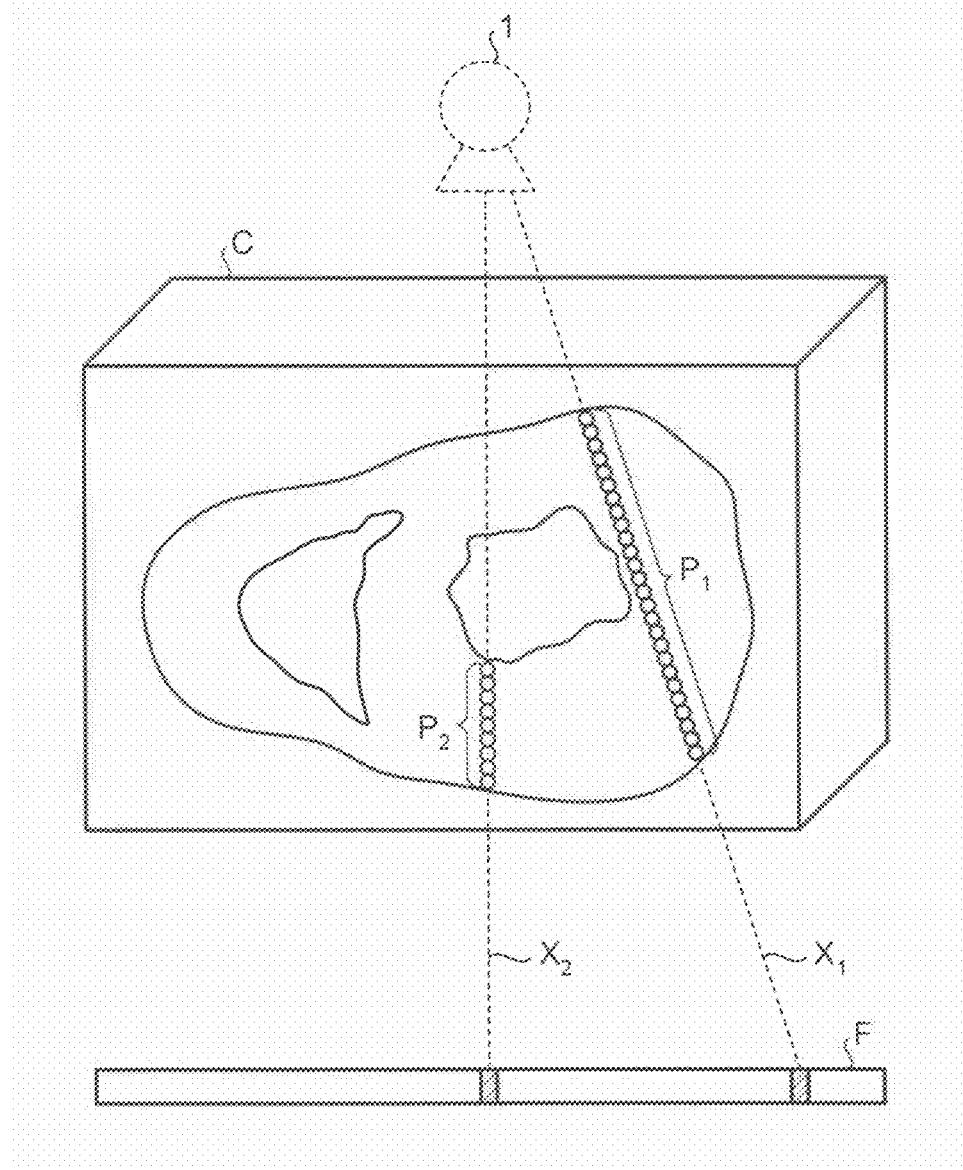

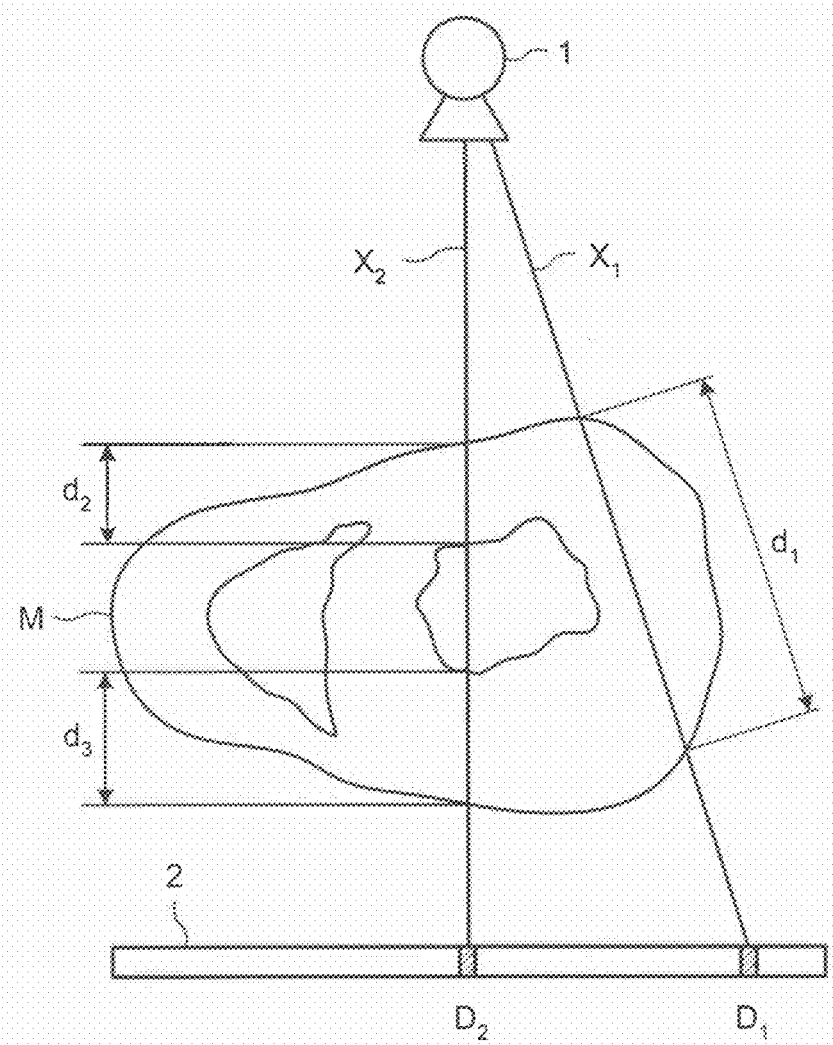

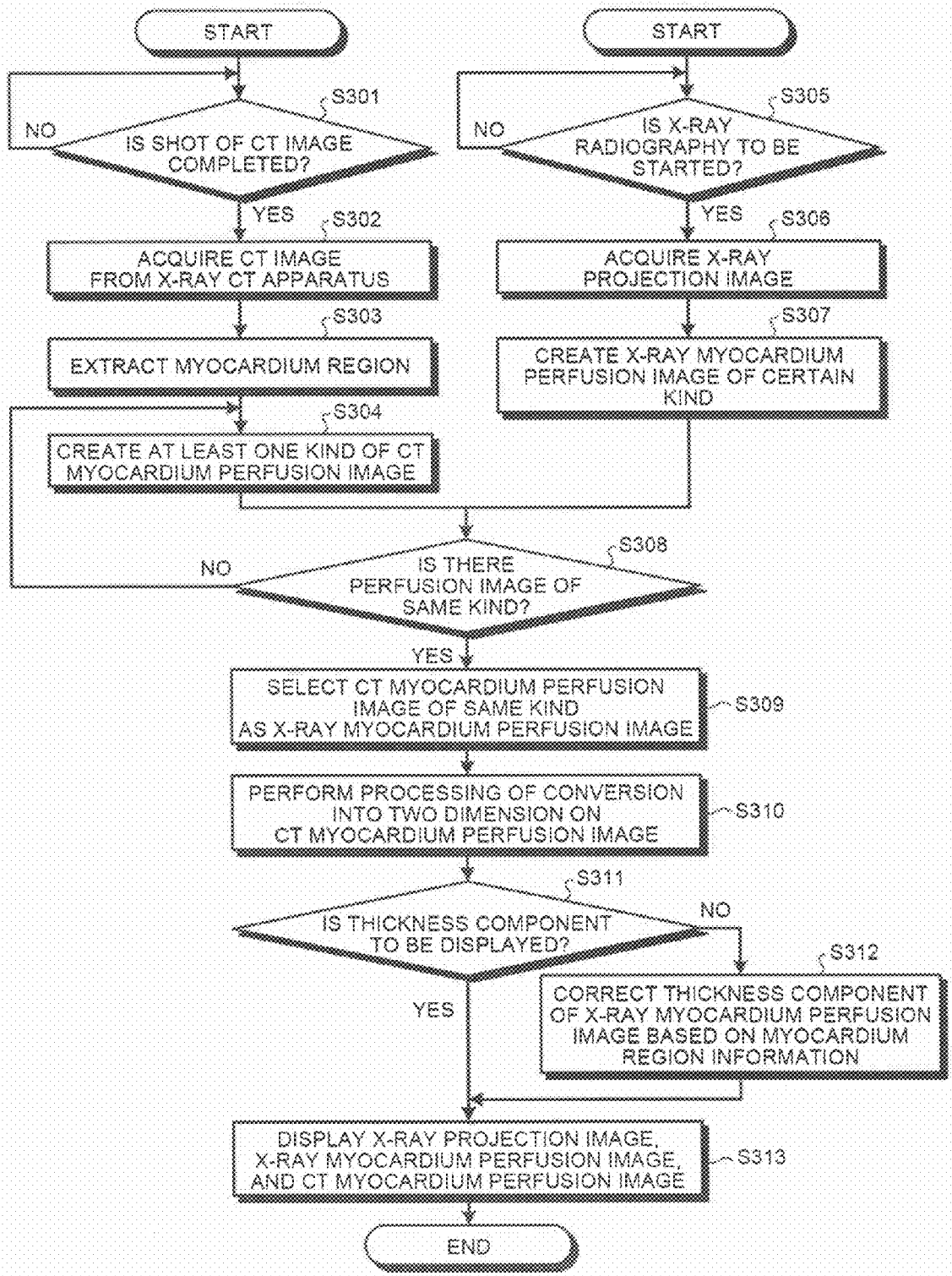

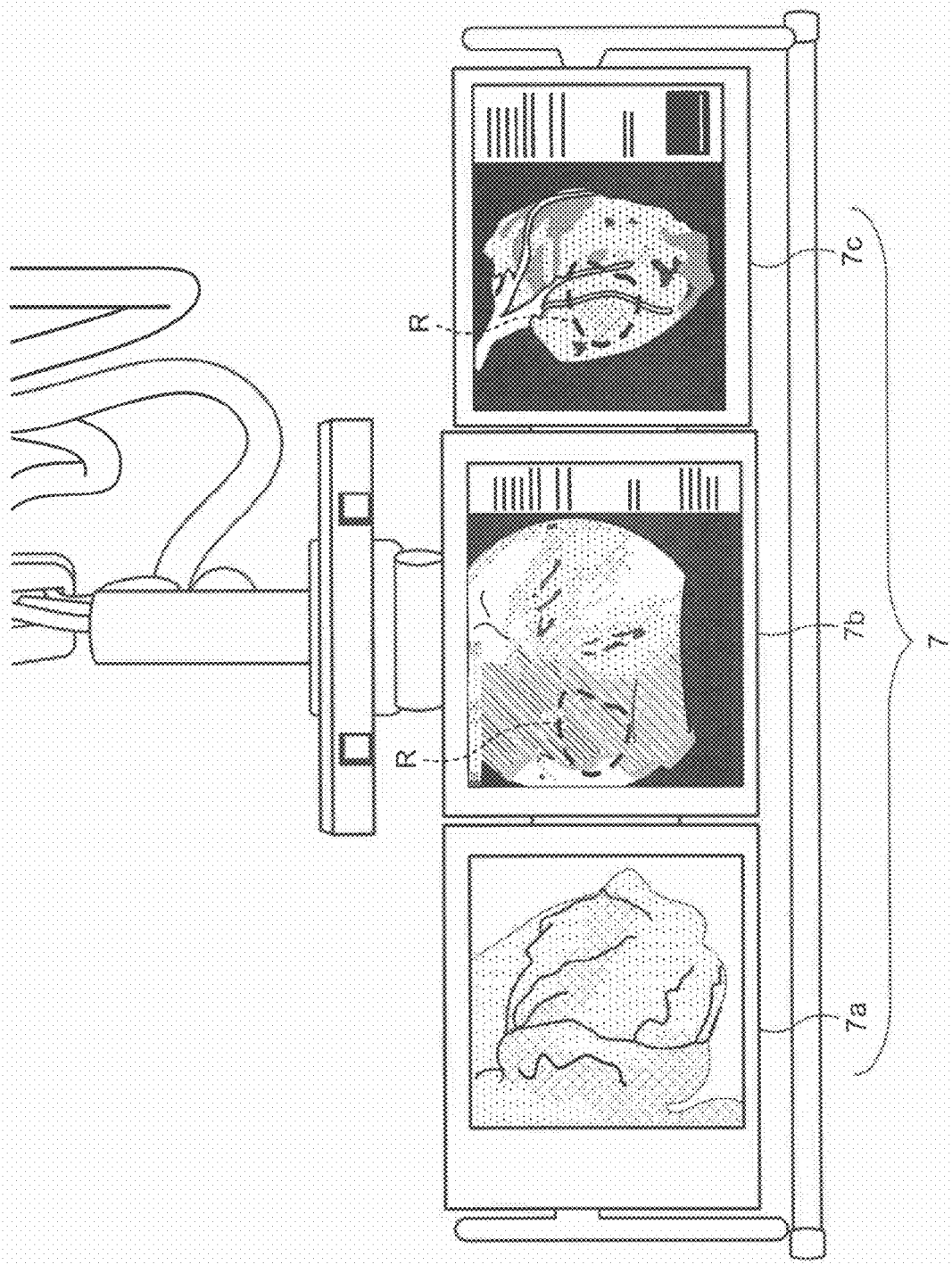

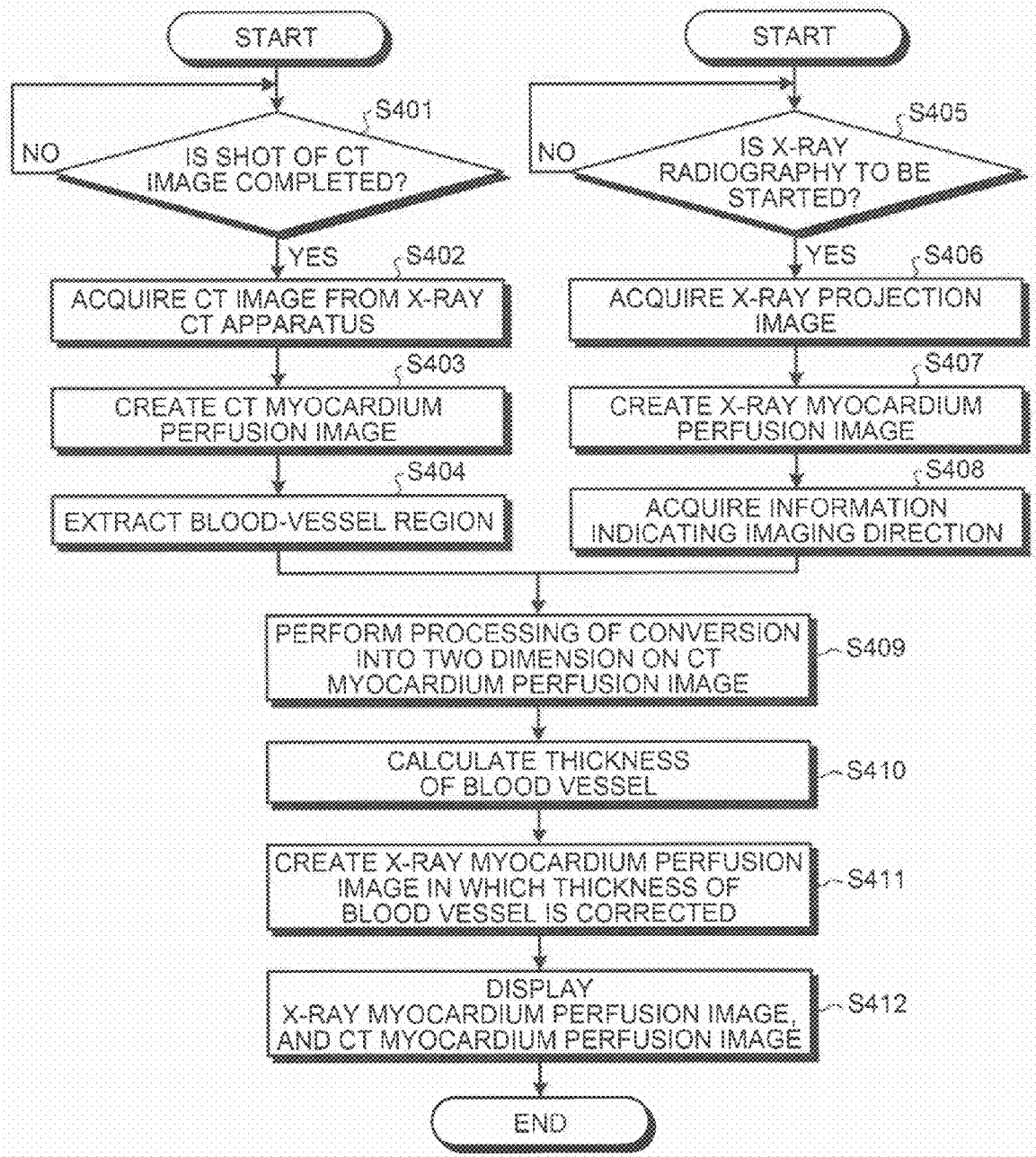

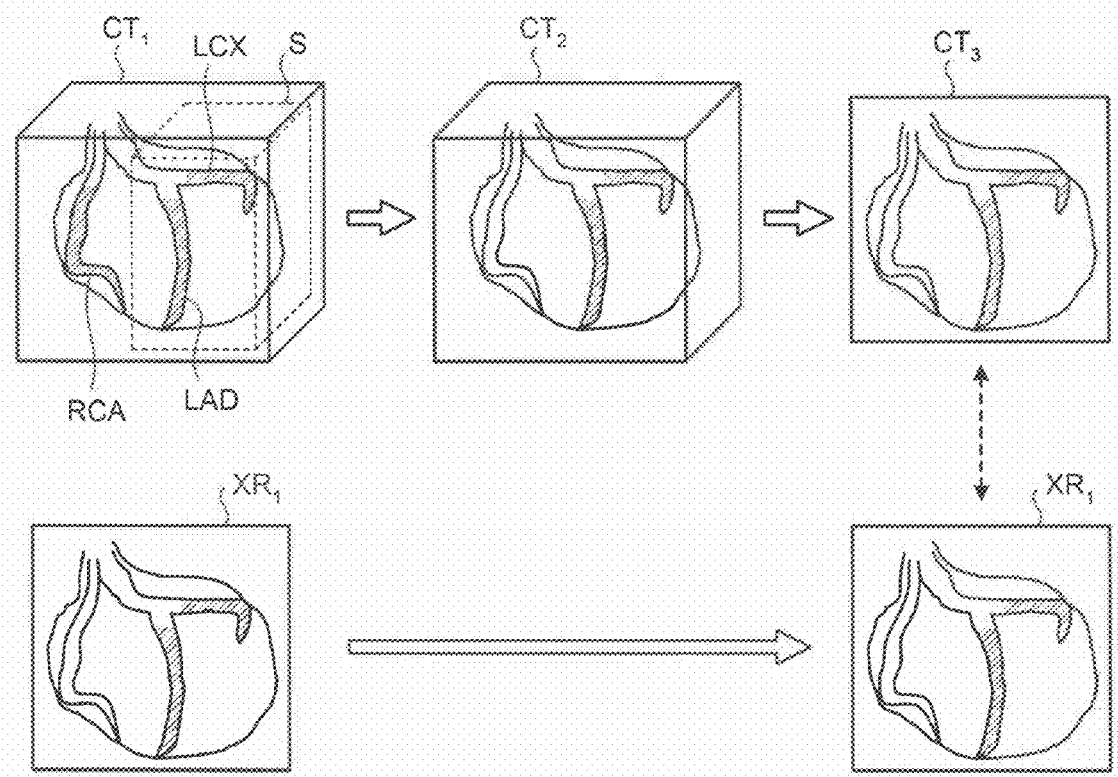

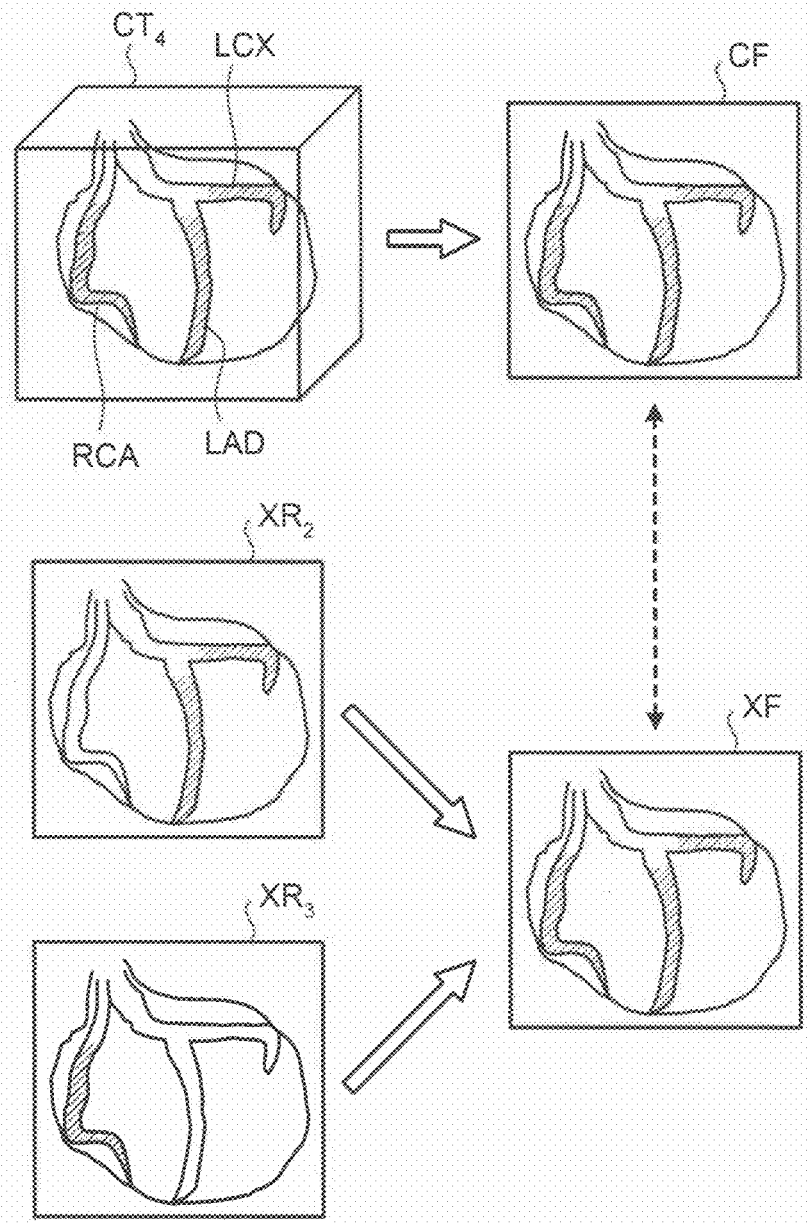

IMAGE DISPLAY APPARATUS AND X-RAY DIAGNOSIS APPARATUS

CROSS-REFERENCE TO RELATED APPLICATIONS

This application is based upon and claims the benefit of priority from the prior Japanese Patent Application No. 2009-109347, filed on Apr. 28, 2009; and Japanese Patent Application No. 2010-059785, filed on Mar. 16, 2010, the entire contents of both of which are incorporated herein by reference.

BACKGROUND OF THE INVENTION

1. Field of the Invention

The present invention relates to an image display apparatus and an X-ray diagnosis apparatus.

2. Description of the Related Art

Conventionally, in an examination of an ischemic heart disease in a field of cardiovascular internal medicine, a diagnosis is performed at first by an X-ray Computed Tomography (CT) apparatus, and when it is diagnosed that a treatment is needed, a treatment is generally performed by using an X-ray diagnosis apparatus. When performing the treatment, strategy of treatment are considered by comparing a myocardium perfusion image created from a CT image taken by the X-ray CT apparatus, and a myocardium perfusion image created from an X-ray projection image taken by the X-ray diagnosis apparatus.

The "myocardium perfusion image" is an image that indicates blood flow dynamics in a myocardium. Such myocardium perfusion image is created by creating a Time Density Curve (TDC) from images that are taken while injecting an iodine contrast agent into a blood vessel, and analyzing the created TDC (for example, see JP-A 2008-136800 (KO-KAI)).

However, a myocardium perfusion image of a CT image and a myocardium perfusion image of an X-ray projection image are different images from each other. Moreover, there is a plurality of kinds of index values indicating the blood flow dynamics described above, and substantially different kinds of perfusion images are created depending on the index value. For this reason, there is a problem that it is very difficult for a doctor to compare the respective perfusion images when performing a treatment.

Recently, a myocardium perfusion image can be created also from an image taken by one of various diagnostic imaging apparatuses, such as a Magnetic Resonance Imaging (MRI) apparatus, and a Positron Emission Tomography (PET) apparatus, as well as an X-ray CT apparatus or an X-ray diagnosis apparatus. The problem described above arises not only in a case of comparing a myocardium perfusion image of a CT image, but also similarly arises in a case of comparing a myocardium perfusion image of an image taken by one of various diagnostic imaging apparatuses, with a myocardium perfusion image of an X-ray projection image.

SUMMARY OF THE INVENTION

According to one aspect of the present invention, an image display apparatus includes an X-ray perfusion-image creating unit that creates an X-ray perfusion image indicating blood flow dynamics in a certain organ from an X-ray projection image of a subject given with a contrast agent; a thickness-information extracting unit that extracts thickness information indicating a thickness of tissue of the organ from a three-dimensional image taken by a diagnostic imaging apparatus; a correction-image creating unit that creates a corrected perfusion image in which a thickness of the tissue of the organ in the X-ray perfusion image is corrected, based on the thickness information; and a display unit that displays the corrected perfusion image.

According to another aspect of the present invention, an image display apparatus includes a diagnosis perfusion-image creating unit that creates a diagnosis perfusion image indicating blood flow dynamics in a certain organ from a three-dimensional image taken by a diagnostic imaging apparatus; a thickness-information extracting unit that extracts thickness information indicating a thickness of tissue of the organ from the three-dimensional image; a correction-image creating unit that creates a corrected perfusion image in which a thickness of the tissue of the organ in the diagnosis perfusion image is corrected, based on the thickness information; and a display unit that displays the corrected perfusion image.

According to still another aspect of the present invention, an image display apparatus includes an X-ray perfusion-image creating unit that creates an X-ray perfusion image indicating blood flow dynamics in a certain organ from an X-ray projection image of a subject given with a contrast agent; a blood-vessel region extracting unit that extracts a region including a blood vessel as a blood vessel region from a three-dimensional image taken by a diagnostic imaging apparatus; a blood-vessel thickness calculating unit that calculates a thickness of the blood vessel in the blood vessel region; a correction-image creating unit that creates a blood-vessel corrected perfusion image in which a thickness of the blood vessel in the X-ray perfusion image is corrected, based on the thickness of the blood vessel calculated by the blood-vessel thickness calculating unit; and a display unit that displays the blood-vessel corrected perfusion image.

According to still another aspect of the present invention, an X-ray diagnosis apparatus includes an X-ray generating unit that generates an X-ray; an X-ray image creating unit that creates an X-ray projection image by detecting X-rays passing through a subject given with a contrast agent; an X-ray perfusion-image creating unit that creates an X-ray perfusion image indicating blood flow dynamics in a certain organ from the X-ray projection image; a thickness-information extracting unit that extracts thickness information indicating a thickness of tissue of the organ from a three-dimensional image taken by a diagnostic imaging apparatus; a correction-image creating unit that creates a corrected perfusion image in which a thickness of the tissue of the organ in the X-ray perfusion image is corrected, based on the thickness information; and a display unit that displays the corrected perfusion image.

According to still another aspect of the present invention, an X-ray diagnosis apparatus includes an X-ray generating unit that generates an X-ray; an X-ray image creating unit that creates an X-ray projection image by detecting X-rays passing through a subject given with a contrast agent; a diagnosis perfusion-image creating unit that creates a diagnosis perfusion image indicating blood flow dynamics in a certain organ from a three-dimensional image taken by a diagnostic imaging apparatus; a thickness-information extracting unit that extracts thickness information indicating a thickness of tissue of the organ from the three-dimensional image; a correction-image creating unit that creates a corrected perfusion image in which a thickness of the tissue of the organ in the diagnosis perfusion image is corrected, based on the thickness information; and a display unit that displays the X-ray projection image and the corrected perfusion image.

According to still another aspect of the present invention, an X-ray diagnosis apparatus includes an X-ray generating unit that generates an X-ray; an X-ray image creating unit that creates an X-ray projection image by detecting X-rays passing through a subject given with a contrast agent; an X-ray perfusion-image creating unit that creates an X-ray perfusion image indicating blood flow dynamics in a certain organ from the X-ray projection image; a blood-vessel region extracting unit that extracts a region including a blood vessel as a blood vessel region from a three-dimensional image taken by a diagnostic imaging apparatus; a blood-vessel thickness calculating unit that calculates a thickness of the blood vessel in the blood vessel region; a correction-image creating unit that creates a blood-vessel corrected perfusion image in which a thickness of the blood vessel in the X-ray perfusion image is corrected, based on the thickness of the blood vessel calculated by the blood-vessel thickness calculating unit; and a display unit that displays the blood-vessel corrected perfusion image.

BRIEF DESCRIPTION OF THE DRAWINGS

FIG. 6 is a flowchart of a flow of image display by the X-ray diagnosis apparatus according to the second embodiment;

FIG. 7 is a schematic diagram that depicts an example of correction of a Computed Tomography (CT) myocardium perfusion image by an image correction unit;

FIG. 8 is a schematic diagram for explaining correction of thickness components by the image correction unit;

FIG. 9 is a flowchart of a flow of image display by an X-ray diagnosis apparatus according to a third embodiment of the present invention;

FIG. 10 is a schematic diagram that depicts an example when displaying an ischemic region in a highlighted manner on an X-ray myocardium perfusion image;

FIG. 11 is a flowchart of a flow of image display by the X-ray diagnosis apparatus according to the third embodiment;

FIGS. 13 and 14 are schematic diagrams that depict an example when correcting a myocardium perfusion image so as to match contrasted blood vessels with each other.

DETAILED DESCRIPTION OF THE INVENTION

Exemplary embodiments of an image display apparatus and an X-ray diagnosis apparatus according to the present invention will be explained below in detail with reference to the accompanying drawings. The present invention is not limited by the embodiments described below.

Before explaining the embodiments according to the present invention, a perfusion image to be used in the following embodiments is explained below. A "perfusion image" is an image indicating blood flow dynamics in a certain organ, and is created by creating a Time Density Curve (TDC) with respect to a certain index value from an image that is taken while injecting an iodine contrast agent into a blood vessel, and analyzing the created TDC. Specifically, a perfusion image is created by setting pixel values to be included in the image in accordance with a certain index value indicating blood flow dynamics.

An index value when creating a perfusion image can be: for example, a certain density value, such as the maximum density value, the minimum density value, or 90% of the maximum density value of the density; a lapse time until reaching a certain density; a Mean transit Time (MTT) of blood; a Blood Flow (BL); a Blood Volume (BV); or a value indicating an inflow state or an outflow state of blood with respect to a certain region. As described above, there is a plurality of kinds corresponding to respective index values indicating blood flow dynamics, and a substantially different kind of perfusion image is created depending on each of the index values.

The following embodiments are explained below in cases where an organ subjected to a diagnosis is a heart, and a myocardium perfusion image of a CT image taken by an X-ray CT apparatus is compared with a myocardium perfusion image of an X-ray projection image taken by an X-ray diagnosis apparatus.

Figure 1:
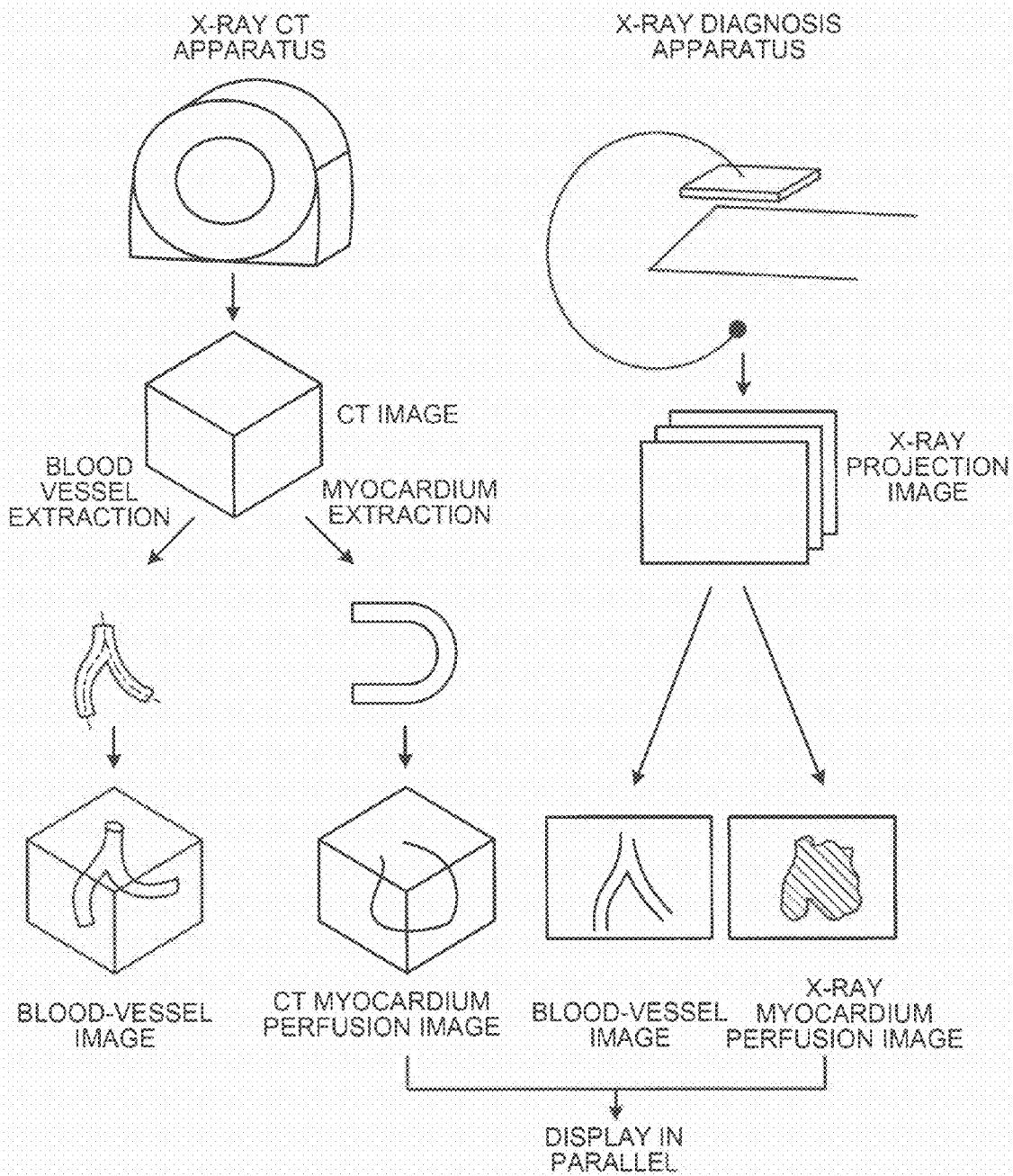
FIG. 1 is a schematic diagram for explaining an outline of an X-ray diagnosis apparatus according to a first embodiment of the present invention.

First of all, an outline of an X-ray diagnosis apparatus according to a first embodiment of the present invention is explained below. FIG. 1 is a schematic diagram for explaining an outline of the X-ray diagnosis apparatus according to the first embodiment. As shown in FIG. 1, the X-ray diagnosis apparatus according to the first embodiment creates a myocardium perfusion image from an X-ray projection image taken by X-ray radiography. Hereinafter, a myocardium perfusion image created from an X-ray projection image is referred to as an "X-ray myocardium perfusion image".

Moreover, the X-ray diagnosis apparatus according to the first embodiment creates at least one kind of myocardium perfusion image from a CT image taken by an X-ray CT apparatus. Hereinafter, a myocardium perfusion image created from a CT image is referred to as a "CT myocardium perfusion image".

When the X-ray diagnosis apparatus according to the first embodiment creates an X-ray myocardium perfusion image, the X-ray diagnosis apparatus selects a myocardium perfusion image of the same kind as the created X-ray myocardium perfusion image from among CT myocardium perfusion images that are already created. The X-ray diagnosis apparatus according to the first embodiment then causes a display unit to display the created X-ray myocardium perfusion image and the CT myocardium perfusion image in parallel.

In this way, according to the first embodiment, it is configured to cause the display unit to display perfusion images of the same kind in parallel, thereby managing to compare a plurality of perfusion images easily, when comparing a perfusion image created from an X-ray projection image and a perfusion image created from a CT image.

Figure 2:
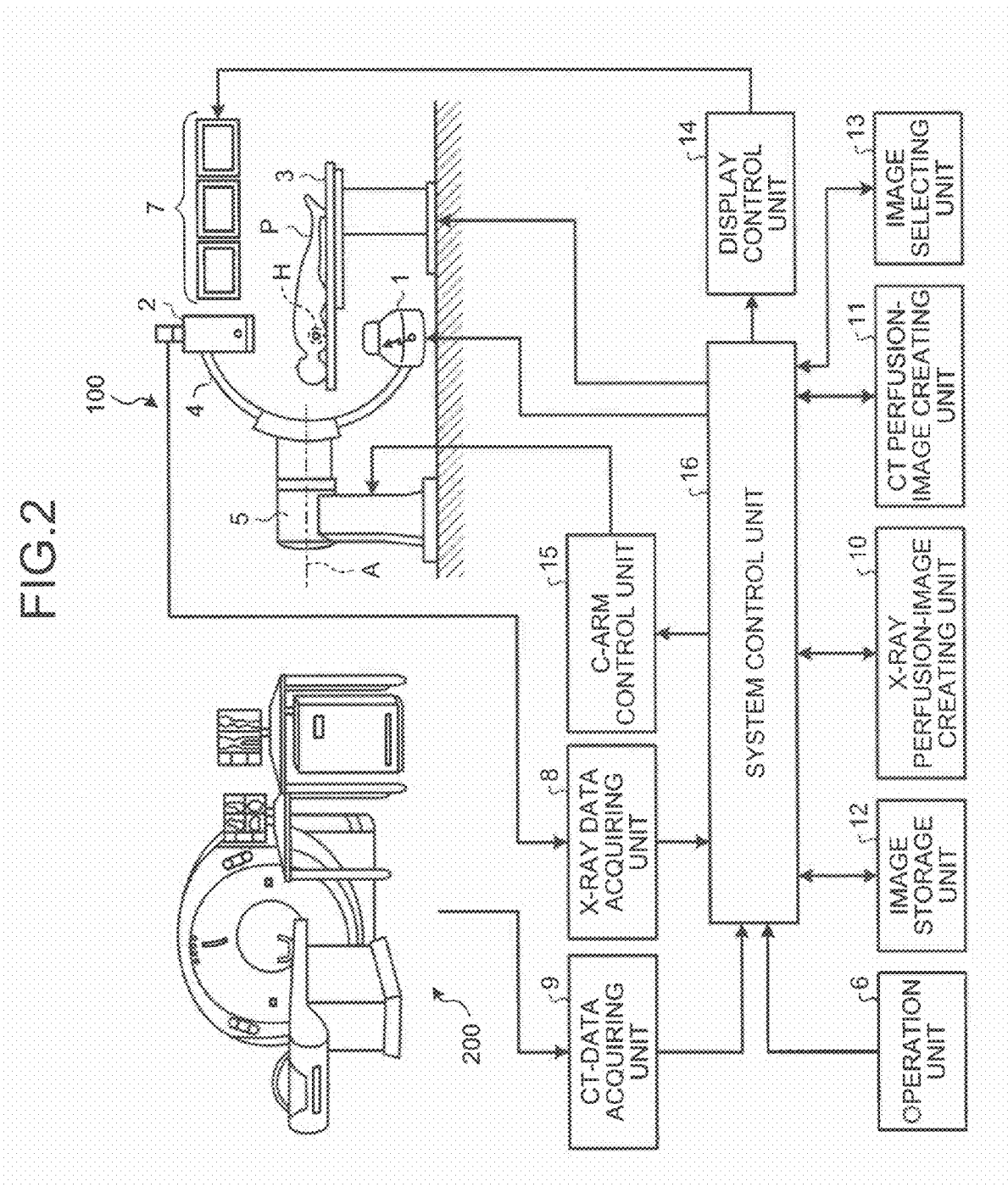
FIG. 2 is a functional block diagram of a configuration of the X-ray diagnosis apparatus according to the first embodiment.

A configuration of the X-ray diagnosis apparatus according to the first embodiment is explained below. FIG. 2 is a functional block diagram of a configuration of an X-ray diagnosis apparatus 100 according to the first embodiment. As shown in FIG. 2, the X-ray diagnosis apparatus 100 according to the first embodiment is connected to an X-ray CT apparatus 200 via a network, for example, a Local Area Network (LAN).

Moreover, the X-ray diagnosis apparatus 100 includes an X-ray generating unit 1, an X-ray detecting unit 2, a couch 3, a C-arm 4, a C-arm rotating/moving mechanism 5, an operation unit 6, a display unit 7, an X-ray data acquiring unit 8, and a CT-data acquiring unit 9. Furthermore, the X-ray diagnosis apparatus 100 includes an X-ray perfusion-image creating unit 10, a CT perfusion-image creating unit 11, an image storage unit 12, an image selecting unit 13, a display control unit 14, a C-arm control unit 15, and a system control unit 16.

The X-ray generating unit 1 generates an X-ray by using a high voltage supplied from a not-shown high-voltage generating unit. The X-ray detecting unit 2 detects an X-ray passing through a subject P. The X-ray detecting unit 2 converts the X-ray passing through the subject P into an electric signal, and creates an X-ray projection image based on the converted electric signal. According to the first embodiment, the X-ray detecting unit 2 creates an X-ray projection image based on an X-ray passing through a heart H of the subject P.

The couch 3 is a bed on which the subject P is to be placed during an examination. The C-arm 4 holds the X-ray generating unit 1 and the X-ray detecting unit 2 so as to be arranged on opposite sides of the subject P placed on the couch 3. The C-arm rotating/moving mechanism 5 turns and moves the C-arm 4. For example, the C-arm rotating/moving mechanism 5 turns the C-arm 4 about a rotational axis A shown in FIG. 2.

The operation unit 6 receives various requests from an operator, such as a doctor or an engineer, who operates the X-ray diagnosis apparatus 100, and transfers the received request to the system control unit 16. The operation unit 6 includes, for example, a mouse, a key board, a button, a track ball, a joy stick, and the like.

The display unit 7 displays various information under the control of the display control unit 14. For example, the display unit 7 displays an image stored in the image storage unit 12, and a Graphical User Interface (GUI) for receiving various operations from the operator via the operation unit 6. The display unit 7 includes a monitor, for example, a liquid crystal display, or a Cathode Ray Tube (CRT) display.

The X-ray data acquiring unit 8 acquires an X-ray projection image created by the X-ray detecting unit 2. The X-ray data acquiring unit 8 then stores the acquired X-ray projection image into the image storage unit 12 time sequentially.

The CT-data acquiring unit 9 acquires a CT image taken by the X-ray CT apparatus 200. The CT-data acquiring unit 9 then stores the acquired CT image into the image storage unit 12 time sequentially. The "CT image" here means a three-dimensional image created by the X-ray CT apparatus 200, i.e., volume data.

The X-ray perfusion-image creating unit 10 creates an X-ray myocardium perfusion image from an X-ray projection image acquired by the X-ray data acquiring unit 8.

Specifically, when the X-ray data acquiring unit 8 acquires an X-ray projection image, the X-ray perfusion-image creating unit 10 reads the acquired X-ray projection image from the image storage unit 12 sequentially. The X-ray perfusion-image creating unit 10 then creates an X-ray myocardium perfusion image from the read X-ray projection image based on a certain kind of index value.

The X-ray perfusion-image creating unit 10 then stores the created X-ray myocardium perfusion image into the image storage unit 12. When storing the X-ray myocardium perfusion image into the image storage unit 12, the X-ray perfusion-image creating unit 10 gives supplementary information including the kind of index value indicating blood flow dynamics to the X-ray myocardium perfusion image, and then stores the X-ray myocardium perfusion image into the image storage unit 12. The supplementary information here includes information about various imaging conditions at a moment of taking an X-ray projection image that is a base of the X-ray myocardium perfusion image, in addition to the kind of index value.

The CT perfusion-image creating unit 11 creates at least one kind of CT myocardium perfusion image from CT images acquired by the CT-data acquiring unit 9.

Specifically, when the CT-data acquiring unit 9 acquires a CT image, the CT perfusion-image creating unit 11 reads the acquired CT image from the image storage unit 12 sequentially. The CT perfusion-image creating unit 11 then creates at least one kind of CT myocardium perfusion image from the read CT image, based on at least one kind of index value.

The CT perfusion-image creating unit 11 then stores the created CT myocardium perfusion image into the image storage unit 12. When storing the CT myocardium perfusion image into the image storage unit 12, the CT perfusion-image creating unit 11 gives supplementary information including the kind of index value indicating blood flow dynamics to the CT myocardium perfusion image, and then stores the CT myocardium perfusion image into the image storage unit 12. The supplementary information here includes information about various imaging conditions at a moment of taking the CT image that is a base of the CT myocardium perfusion image, in addition to the kind of index value.

The image storage unit 12 stores various image data. Specifically, the image storage unit 12 stores an X-ray projection image acquired by the X-ray data acquiring unit 8, CT data acquired by the CT-data acquiring unit 9, an X-ray myocardium perfusion image created by the X-ray perfusion-image creating unit 10, a CT myocardium perfusion image created by the CT perfusion-image creating unit 11, and the like.

The image selecting unit 13, When an X-ray myocardium perfusion image is created by the X-ray perfusion-image creating unit 10, selects a CT myocardium perfusion image of the same kind as the created X-ray myocardium perfusion image from among CT myocardium perfusion images created by the CT perfusion-image creating unit 11.

Specifically, when an X-ray myocardium perfusion image is created by the X-ray perfusion-image creating unit 10, the image selecting unit 13 acquires the created X-ray myocardium perfusion image from the image storage unit 12. The image selecting unit 13 then refers to supplementary information about the X-ray myocardium perfusion image acquired from the image storage unit 12, thereby specifying the kind of index value about the X-ray myocardium perfusion image. The image selecting unit 13 then refers to supplementary information about each of the CT myocardium perfusion images stored in the image storage unit 12, and acquires a CT myocardium perfusion image that is created based on the same kind of index value as the specified kind of index value about the X-ray myocardium perfusion image.

The display control unit 14 causes the display unit 7 to display various images. Specifically, the display control unit 14 causes the display unit 7 to display an X-ray projection image acquired by the X-ray data acquiring unit 8, an X-ray myocardium perfusion image created by the X-ray perfusion-image creating unit 10, and a CT myocardium perfusion image selected by the image selecting unit 13 in parallel.

Figure 3:
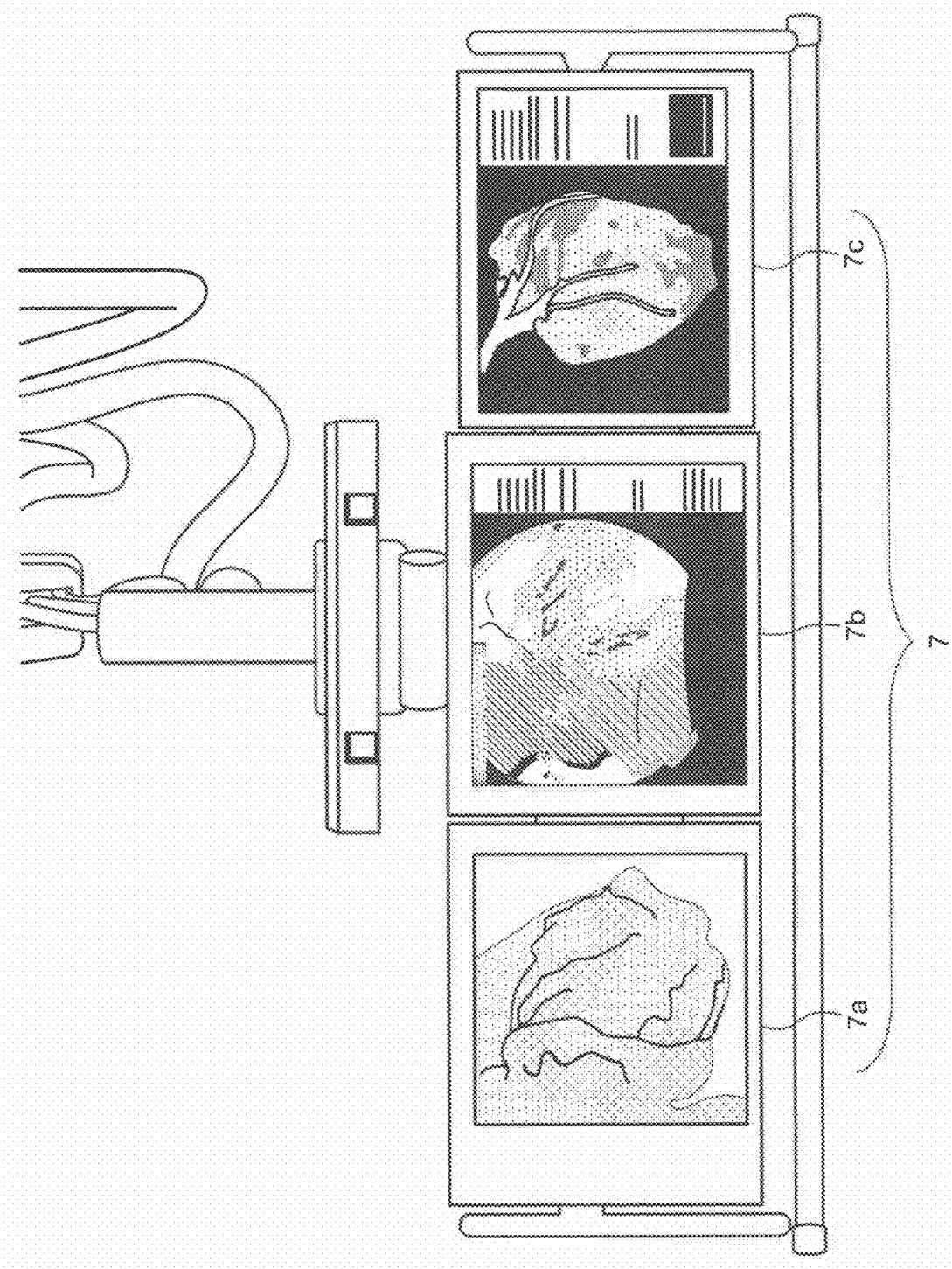
FIG. 3 is a schematic diagram that depicts an example of display of perfusion images by a display control unit.

FIG. 3 is a schematic diagram that depicts an example of display of perfusion images by the display control unit 14. FIG. 3 depicts a case where the display unit 7 includes monitors 7a, 7b, and 7c. For example, as shown in FIG. 3, the display control unit 14 causes the monitor 7a to display an X-ray projection image, causes the monitor 7b to display an X-ray myocardium perfusion image, and causes the monitor 7c to display a CT myocardium perfusion image.

Explained above is a case where the display control unit 14 causes respective separate monitors to display an X-ray projection image, an X-ray myocardium perfusion image, and a CT myocardium perfusion image; however, the present invention is not limited to this. For example, it can be configured such that the display control unit 14 causes one monitor to display all of the three images, or any two of the images.

Returning to FIG. 2, the C-arm control unit 15 performs turn adjustment and movement adjustment of the C-arm 4 by driving the C-arm rotating/moving mechanism 5. For example, as the C-arm control unit 15 performs turn adjustment of the C-arm 4, the X-ray generating unit 1 and the X-ray detecting unit 2 move around the subject P, and the radiation direction of X-rays to be radiated onto the subject P is changed. Accordingly, the imaging direction of an X-ray projection image can be changed.

The system control unit 16 controls operations of the whole of the X-ray diagnosis apparatus 100. Specifically, the system control unit 16 causes the X-ray diagnosis apparatus 100 to function as a single apparatus by performing shift of control between functional units and transfer of data between a functional unit and a storage unit as described above, based on various requests transferred from the operation unit 6.

Figure 4:
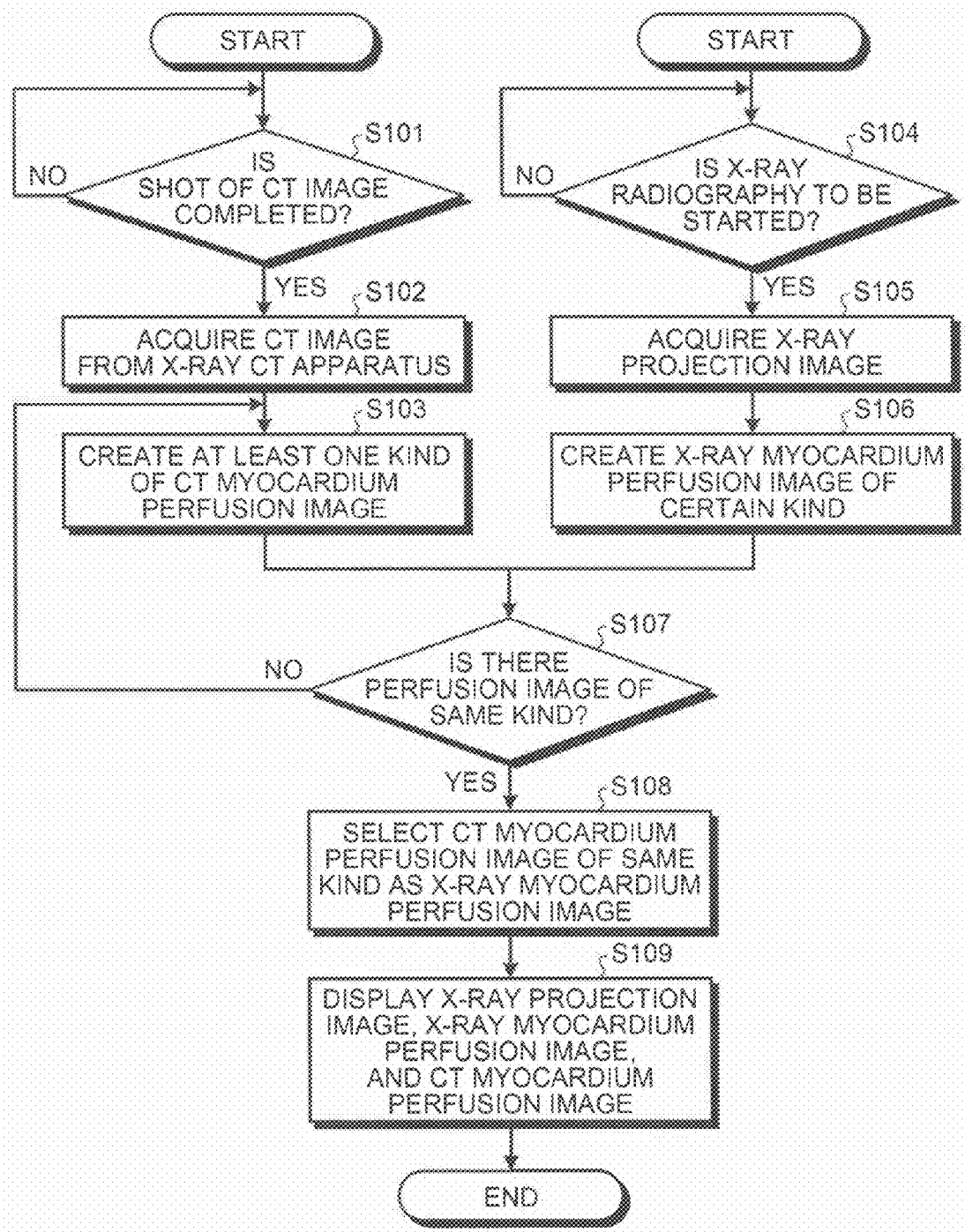
FIG. 4 is a flowchart of a flow of image display by the X-ray diagnosis apparatus according to the first embodiment.

A flow of image display by the X-ray diagnosis apparatus 100 according to the first embodiment is explained below. FIG. 4 is a flowchart of a flow of image display by the X-ray diagnosis apparatus 100 according to the first embodiment.

As shown in FIG. 4, according to the first embodiment, after a CT image is taken by the X-ray CT apparatus 200 (Yes at Step S101); the CT-data acquiring unit 9 acquires the CT image taken by the X-ray CT apparatus 200 (Step S102). Subsequently, the CT perfusion-image creating unit 11 creates at least one kind of CT myocardium perfusion image from the CT image acquired by the CT-data acquiring unit 9 (Step S103).

On the other hand, when the operation unit 6 receives an instruction to start X-ray radiography from the operator (Yes at Step S104); the X-ray data acquiring unit 8 acquires an X-ray projection image created by the X-ray detecting unit 2 (Step S105). Subsequently, the X-ray perfusion-image creating unit 10 creates an X-ray myocardium perfusion image of a certain kind from the X-ray projection image acquired by the X-ray data acquiring unit 8 (Step S106).

When the X-ray myocardium perfusion image is created by the X-ray perfusion-image creating unit 10, the image selecting unit 13 determines whether there is a CT myocardium perfusion image of the same kind as the created X-ray myocardium perfusion image, among the CT myocardium perfusion images created by the CT perfusion-image creating unit 11 (Step S107).

If there is no CT myocardium perfusion image of the same kind as the X-ray myocardium perfusion image (No at Step S107); the image selecting unit 13 instructs the CT perfusion-image creating unit 11 to create a CT myocardium perfusion image of the same kind as the X-ray myocardium perfusion image (going back to Step S103). By contrast, if a CT myocardium perfusion image of the same kind as the X-ray myocardium perfusion image is obtained (Yes at Step S107); the image selecting unit 13 selects the obtained CT myocardium perfusion image (Step S108).

After that, the display control unit 14 causes the display unit 7 to display the X-ray projection image acquired by the X-ray data acquiring unit 8, the X-ray myocardium perfusion image created by the X-ray perfusion-image creating unit 10, and the CT myocardium perfusion image selected by the image selecting unit 13 in parallel (Step S109).

As described above, according to the first embodiment, the X-ray perfusion-image creating unit 10 creates an X-ray myocardium perfusion image from an X-ray projection image taken through X-ray radiography; and the CT perfusion-image creating unit 11 creates at least one kind of CT myocardium perfusion image from a CT image taken by the X-ray CT apparatus 200. When the X-ray myocardium perfusion image is created by the X-ray perfusion-image creating unit 10, the image selecting unit 13 selects a CT myocardium perfusion image of the same kind as the created X-ray myocardium perfusion image, among the CT myocardium perfusion images created by the CT perfusion-image creating unit 11. After that, the display control unit 14 causes the display unit 7 to display the X-ray myocardium perfusion image created by the X-ray perfusion-image creating unit 10, and the CT myocardium perfusion image selected by the image selecting unit 13 in parallel.

Therefore, according to the first embodiment, when comparing a perfusion image created from an X-ray projection image and a perfusion image created from a CT image, a plurality of kinds of perfusion images can be easily compared. Accordingly, a doctor can carry out a diagnosis precisely and promptly. Moreover, a treatment can be efficiently performed by using an X-ray diagnosis apparatus.

Although the first embodiment is explained above in a case of creating a myocardium perfusion image based on a certain index value, the present invention is not limited to this. For example, it can be configured to create a relative value image with respect to a certain index value as a myocardium perfusion image. The relative value image here can be a relative value (a relative value image) of a perfusion value in an ischemic region relative to a perfusion value in a normal region, a relative value (a relative value image) in each region relative to an average perfusion value in an image, a relative value (a relative value image) of a perfusion value at rest relative to a perfusion value under a stress caused by, for example, adenosine, or the like.

In such case, specifically, the CT perfusion-image creating unit 11 creates a CT myocardium perfusion image so as to match a range of an index value in the X-ray myocardium perfusion image created by the X-ray perfusion-image creating unit 10 with a range of the index value in the CT myocardium perfusion image.

Suppose, for example, a range of a certain index value in the X-ray myocardium perfusion image created by the X-ray perfusion-image creating unit 10 is from 0 to 20. As a result of creating a perfusion image by the CT perfusion-image creating unit 11 based on the same index value from a CT image acquired by the CT-data acquiring unit 9, suppose that a range of the index value in the created perfusion image is from 0 to 40. In such case, the CT perfusion-image creating unit 11 creates as a CT myocardium perfusion image a relative value image that each index value is converted to match with the range of the index value in the X-ray myocardium perfusion image, by multiplying each index value in the CT myocardium perfusion image by 0.5 (=20/40).

Accordingly, the respective ranges of index value in the X-ray myocardium perfusion image and the CT myocardium perfusion image match to each other, so that myocardium perfusion images can be compared to each other more accurately. Moreover, in each of the myocardium perfusion images, a region in which a blood supply is sufficient and a region in which a blood supply is insufficient can be easily divided.

When it is assumed that the myocardium perfusion image explained in the first embodiment is an absolute value image, and the myocardium perfusion image explained above is a relative value image; it can be configured such that the X-ray perfusion-image creating unit 10 creates either an absolute value image or a relative value image, and the CT perfusion-image creating unit 11 creates both an absolute value image and a relative value image. In such case, when an absolute value image is created by the X-ray perfusion-image creating unit 10, the image selecting unit 13 selects an absolute value image created by the CT perfusion-image creating unit 11. By contrast, when a relative value image is created by the X-ray perfusion-image creating unit 10, the image selecting unit 13 selects a relative value image created by the CT perfusion-image creating unit 11.

Moreover, the first embodiment is explained above in a case where a CT myocardium perfusion image of the same kind as an X-ray myocardium perfusion image is selected from among at least one kind of CT myocardium perfusion images, and displayed together with the X-ray myocardium perfusion image; however, the present invention is not limited to this. For example, it can be configured to select a CT myocardium perfusion image from among a plurality of kinds of CT images, such as a CT myocardium perfusion image and a CT blood-vessel image, and to display it together with an X-ray myocardium perfusion image.

In such case, specifically, the X-ray perfusion-image creating unit 10 creates an X-ray myocardium perfusion image from an X-ray projection image taken by X-ray radiography. Additionally, the CT perfusion-image creating unit 11 creates a plurality kinds of CT images including a CT myocardium perfusion image from CT images taken by the X-ray CT apparatus 200. Furthermore, the image selecting unit 13 selects a CT myocardium perfusion image from among the plurality of kinds of CT images created by the CT perfusion-image creating unit 11. The display control unit 14 then causes the display unit 7 to display the X-ray myocardium perfusion image created by the X-ray perfusion-image creating unit 10, and the CT myocardium perfusion image selected by the image selecting unit 13 in parallel.

Accordingly, even when various kinds of CT images are created in addition to a CT myocardium perfusion image, a CT myocardium perfusion image is automatically selected and displayed together with an X-ray myocardium perfusion image, so that the X-ray myocardium perfusion image and the CT myocardium perfusion image can be easily compared with each other.

Furthermore, the first embodiment is explained above in a case of displaying a CT myocardium perfusion image of the same kind as an X-ray myocardium perfusion image; however, the present invention is not limited to this. For example, when displaying a CT myocardium perfusion image, furthermore, it can be configured to correct the CT myocardium perfusion image, so as to display an X-ray myocardium perfusion image and the CT myocardium perfusion image in the same display mode. Therefore, a case of correcting a CT myocardium perfusion image is explained below as a second embodiment of the present invention.

Figure 5:
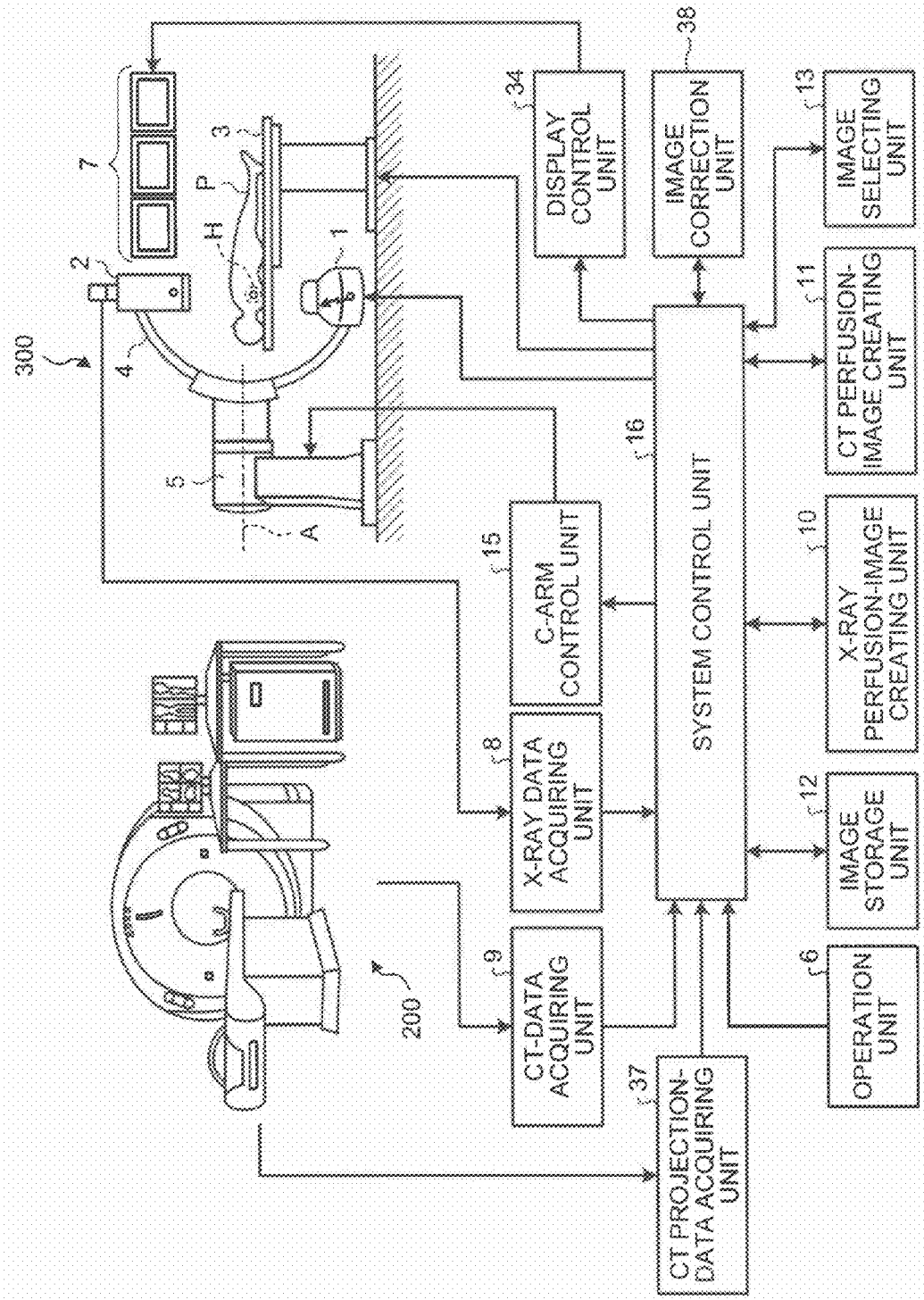
FIG. 5 is a functional block diagram of a configuration of an X-ray diagnosis apparatus according to a second embodiment of the present invention.

At first, a configuration of an X-ray diagnosis apparatus according to the second embodiment is explained below. FIG. 5 is a functional block diagram of a configuration of an X-ray diagnosis apparatus 300 according to the second embodiment. For convenience of explanations, functional units that have the same functions as the units shown in FIG. 2 have are assigned with the same reference numerals, and detailed explanations of them are omitted.

As shown in FIG. 5, the X-ray diagnosis apparatus 300 according to the second embodiment includes the X-ray generating unit 1, the X-ray detecting unit 2, the couch 3, the C-arm 4, the C-arm rotating/moving mechanism 5, the operation unit 6, the display unit 7, the X-ray data acquiring unit 8, and the CT-data acquiring unit 9. Moreover, the X-ray diagnosis apparatus 300 includes the X-ray perfusion-image creating unit 10, the CT perfusion-image creating unit 11, the image storage unit 12, the image selecting unit 13, a display control unit 34, the C-arm control unit 15, and the system control unit 16. Furthermore, the X-ray diagnosis apparatus 300 includes a CT projection-data acquiring unit 37, and an image correction unit 38.

The CT projection-data acquiring unit 37 acquires projection data needed at a moment when reconstructing a CT image taken by the X-ray CT apparatus 200. Specifically, the CT projection-data acquiring unit 37 acquires projection data collected by the X-ray CT apparatus 200, under the control of the image correction unit 38.

The image correction unit 38 corrects a CT myocardium perfusion image selected by the image selecting unit 13 so as to be displayed in the same display mode as the X-ray myocardium perfusion image. Specifically, the image correction unit 38 corrects the CT myocardium perfusion image so as to display both the X-ray myocardium perfusion image and the CT myocardium perfusion image in the same display mode, based on supplementary information given to each of the images. At that moment, the image correction unit 38 acquires a CT image needed for correction from among CT images stored in the image storage unit 12.

For example, the image correction unit 38 corrects a CT myocardium perfusion image so as to be displayed in the same direction as the X-ray myocardium perfusion image. An X-ray projection image created by the X-ray detecting unit 2 is a two-dimensional image because it is created by detecting photons passing through the subject P from the X-ray generating unit 1. On the other hand, a CT image is a three-dimensional image. Therefore, the image correction unit 38 creates a projection image by turning the CT myocardium perfusion image so as to be in the same direction as the X-ray projection image is taken.

Moreover, for example, the image correction unit 38 corrects the CT myocardium perfusion image so as to be displayed in the same magnification as the X-ray myocardium perfusion image. In such case, the image correction unit 38 enlarges or reduces the size of the CT myocardium perfusion image so as to have the same ratio of a distance between the X-ray generating unit 1 and the X-ray detecting unit 2 to a distance between the X-ray generating unit 1 and the subject P.

Furthermore, for example, the image correction unit 38 corrects the CT myocardium perfusion image so as to be displayed in the same positional relation as the X-ray myocardium perfusion image. Usually, the position of the subject P is slightly shifted between the moment when the subject P is radiographed by the X-ray CT apparatus 200 and the moment when the subject P is radiographed by the X-ray diagnosis apparatus 100. Therefore, the image correction unit 38 adjusts a display position of the CT myocardium perfusion image such that the organ is to be rendered at the same position on the X-ray myocardium perfusion image and the CT myocardium perfusion image. Moreover, the image correction unit 38 deforms the CT myocardium perfusion image if required.

Furthermore, for example, when a diagnosis subject is an organ that moves periodically, the image correction unit 38 corrects the CT myocardium perfusion image so as to have the same movement phase of the organ as the X-ray myocardium perfusion image. For example, when a diagnosis subject is a heart, and when a myocardium in diastole is displayed on the X-ray myocardium perfusion image, the image correction unit 38 corrects the CT myocardium perfusion image so as to display the myocardium in diastole.

When a CT image needed for the correction described above is not stored in the image storage unit 12, the image correction unit 38 reconstructs a CT image needed for the correction from projection data acquired by the CT projection-data acquiring unit 37, and corrects the CT myocardium perfusion image by using the reconstructed image.

Specifically, when a CT image needed for the correction described above is not stored in the image storage unit 12, the image correction unit 38 controls the CT projection-data acquiring unit 37, and acquires projection data to be a base of a CT image needed for the correction from the X-ray CT apparatus 200. The image correction unit 38 then reconstructs a CT image from the acquired projection data, and performs the correction described above by using the reconstructed CT image.

For example, when there is no CT image in the same direction as the X-ray projection image, the image correction unit 38 reconstructs a CT image in the direction. In such case, the image correction unit 38 can be configured to create a CT image in the same direction as the X-ray projection image by matching the angle of already-reconstructed CT volume data with the same direction as the X-ray projection image, and performing processing of conversion into two dimension on the CT volume data. Moreover, when a diagnosis subject is a heart, and when a CT image in a dynamic phase of the X-ray myocardium perfusion image is not stored in the image storage unit 12, the image correction unit 38 reconstructs a CT image in the dynamic phase.

The display control unit 34 causes the display unit 7 to display various images. Specifically, the display control unit 34 causes the display unit 7 to display the X-ray projection image acquired by the X-ray data acquiring unit 8, the X-ray myocardium perfusion image created by the X-ray perfusion-image creating unit 10, and the CT myocardium perfusion image corrected by the image correction unit 38 in parallel.

A flow of image display by the X-ray diagnosis apparatus 300 according to the second embodiment is explained below. FIG. 6 is a flowchart of a flow of image display by the X-ray diagnosis apparatus 300 according to the second embodiment. Processing at Steps S201 to S208 in FIG. 6 is similar to the processing at Steps S101 to S108 shown in FIG. 4, therefore explanations of them are omitted.

As shown in FIG. 6, according to the second embodiment, after the image selecting unit 13 selects a CT myocardium perfusion image of the same kind as an X-ray myocardium perfusion image, the image correction unit 38 determines whether to correct the CT myocardium perfusion image so as to display the X-ray myocardium perfusion image and the CT myocardium perfusion image in the same display mode (Step S209). At that moment, for example, the image correction unit 38 receives from the operator an operation of selecting whether to correct the CT myocardium perfusion image, and determines necessity of correction in accordance with the received operation.

After that, if it is determined not to correct the CT myocardium perfusion image (No at Step S209); the display control unit 14 causes the display unit 7 to display the X-ray projection image acquired by the X-ray data acquiring unit 8, the X-ray myocardium perfusion image created by the X-ray perfusion-image creating unit 10, and the CT myocardium perfusion image selected by the image selecting unit 13 in parallel (Step S216).

By contrast, if it is determined to correct the CT myocardium perfusion image (Yes at Step S209); the image correction unit 38 determines whether there is a CT myocardium perfusion image needed for correction among the CT myocardium perfusion images created by the CT perfusion-image creating unit 11 (Step S210). At that moment, for example, the image correction unit 38 determines whether there is a CT myocardium perfusion image of which imaging direction is the same direction as the X-ray myocardium perfusion image created by the X-ray perfusion-image creating unit 10.

If there is a CT myocardium perfusion image needed for correction (Yes at Step S210); the image correction unit 38 corrects the CT myocardium perfusion image (Step S215). The display control unit 14 then causes the display unit 7 to display the X-ray projection image acquired by the X-ray data acquiring unit 8, the X-ray myocardium perfusion image created by the X-ray perfusion-image creating unit 10, and the CT myocardium perfusion image corrected by the image correction unit 38 in parallel (Step S216).

By contrast, if there is no CT myocardium perfusion image needed for correction (No at Step S210); the image correction unit 38 determines whether a CT image to be a base of the CT myocardium perfusion image is stored in the image storage unit 12 (Step S211). At that moment, for example, the image correction unit 38 determines whether a CT image in the same dynamic phase as the X-ray myocardium perfusion image created by the X-ray perfusion-image creating unit 10 is stored in the image storage unit 12.

If the CT image to be a base of the CT myocardium perfusion image needed for correction is stored in the image storage unit 12 (Yes at Step S211); the image correction unit 38 instructs the CT perfusion-image creating unit 11 to create a CT myocardium perfusion image from the CT image (Step S214). The image correction unit 38 then corrects the CT myocardium perfusion image created by the CT perfusion-image creating unit 11 (Step S215). The display control unit 14 then causes the display unit 7 to display the X-ray projection image acquired by the X-ray data acquiring unit 8, the X-ray myocardium perfusion image created by the X-ray perfusion-image creating unit 10, and the CT myocardium perfusion image corrected by the image correction unit 38 in parallel (Step S216).

By contrast, if the CT image to be a base of the CT myocardium perfusion image needed for correction is not stored in the image storage unit 12 (No at Step S211); the image correction unit 38 controls the CT projection-data acquiring unit 37, and acquires projection data to be a base of a CT image needed for correction from the X-ray CT apparatus 200 (Step S212). Subsequently, the image correction unit 38 reconstructs a CT image from the acquired projection data (Step S213); and creates a CT myocardium perfusion image from the reconstructed CT image (Step S214). The image correction unit 38 then corrects the created CT myocardium perfusion image (Step S215). The display control unit 14 then causes the display unit 7 to display the X-ray projection image acquired by the X-ray data acquiring unit 8, the X-ray myocardium perfusion image created by the X-ray perfusion-image creating unit 10, and the CT myocardium perfusion image corrected by the image correction unit 38 in parallel (Step S216).

As described above, according to the second embodiment, the image correction unit 38 corrects a CT myocardium perfusion image selected by the image selecting unit 13 such that an X-ray myocardium perfusion image and the CT myocardium perfusion image are displayed in the same display mode. The display control unit 34 then causes the display unit 7 to display the X-ray myocardium perfusion image and the CT myocardium perfusion image corrected by the image correction unit 38 in parallel.

Therefore, according to the second embodiment, because the X-ray myocardium perfusion image and the CT myocardium perfusion image are displayed in the same mode, each of the myocardium perfusion images can be efficiently compared.

Moreover, according to the second embodiment, the CT projection-data acquiring unit 37 acquires projection data to be needed when reconstructing a CT image taken by the X-ray CT apparatus 200. If a CT image needed for correction of a CT myocardium perfusion image is not acquired by the CT-data acquiring unit 9, the image correction unit 38 then reconstructs a CT image needed for the correction, and corrects the CT myocardium perfusion image by using the reconstructed CT image.

Therefore, according to the second embodiment, it does not need to create all kinds of CT myocardium perfusion images, so that a storage capacity for storing CT myocardium perfusion images can be saved.

Although according to the second embodiment, explained above is a case of adjusting a display position of a CT myocardium perfusion image so as to render an organ at the same position on both of an X-ray myocardium perfusion image and the CT myocardium perfusion image, sometimes the whole of an organ is not clearly rendered on a perfusion image in some cases. Therefore, for example, it can be configured to perform positioning by using an image of a blood vessel (hereinafter, "blood-vessel image") that is rendered relatively clearly compared with the whole of the organ.

In such case, for example, the X-ray perfusion-image creating unit 10 creates a blood-vessel image based on an X-ray projection image when creating an X-ray myocardium perfusion image, and the CT perfusion-image creating unit 11 creates a blood-vessel image based on a CT image when creating a CT myocardium perfusion image. The image correction unit 38 then adjusts the display position of the CT myocardium perfusion image, based on positional relation about the blood vessel on the respective blood-vessel images created by the X-ray perfusion-image creating unit 10 and the CT perfusion-image creating unit 11.

Accordingly, the X-ray myocardium perfusion image and the CT myocardium perfusion image can be more accurately positioned, and the myocardium perfusion images can be compared with each other further accurately.

Usually, an image taken by an X-ray diagnosis apparatus is a projection image. The projection image is obtained by detecting photons passing through the subject with an X-ray detecting unit. For this reason, for example, when radiographing a heart, an integrated value of the amount of absorption of photons passing through a myocardium is to be imaged. Therefore, when an X-ray myocardium perfusion image is created from a projection image taken by the X-ray diagnosis apparatus, the created X-ray myocardium perfusion image includes a thickness component of the myocardium in the projection direction.

Specifically, a pixel indicating a portion in which the myocardium is thick along the projection direction has a large perfusion value, and a pixel indicating a portion in which the myocardium is thin along the projection direction has a small perfusion value. Accordingly, when observing a diseased part by using an X-ray myocardium perfusion image, there is no problem in a region onto which an X-ray is perpendicularly radiated because the region is correctly imaged; however, about a region onto which an X-ray is diagonally radiated, a thickness component needs to be taken into account.

By contrast, a CT image taken by an X-ray CT apparatus is a three-dimensional image, so that a perfusion image created from the CT image is also a three-dimensional image. For this reason, it can be configured to extract information indicating thickness of organ tissue from a CT image, and to correct a thickness component of the myocardium included in an X-ray myocardium perfusion image or a CT myocardium perfusion image, based on the extracted information. Therefore, a case of correcting a thickness component of a myocardium included in an X-ray myocardium perfusion image or a CT myocardium perfusion image is explained below as a third embodiment of the present invention.

A configuration of an X-ray diagnosis apparatus according to the third embodiment is basically the same as the configuration of the X-ray diagnosis apparatus 300 shown in FIG. 5, and only different in processing to be performed by the CT perfusion-image creating unit 11 and the image correction unit 38. Therefore, mainly, processing to be performed by the CT perfusion-image creating unit 11 and the image correction unit 38 according to the third embodiment is explained below.

According to the third embodiment, the CT perfusion-image creating unit 11 creates a CT myocardium perfusion image similarly to the second embodiment, and extracts myocardium region information indicating a region occupied by a myocardium from a CT image acquired by the CT-data acquiring unit 9.

According to the third embodiment, the image correction unit 38 corrects either an X-ray myocardium perfusion image created by the X-ray perfusion-image creating unit 10 or a CT myocardium perfusion image created by the CT perfusion-image creating unit 11, so as to match respective thickness components included in the X-ray myocardium perfusion image and the CT myocardium perfusion image with each other, based on the myocardium region information extracted by the CT perfusion-image creating unit 11.

When correcting, as explained below, the image correction unit 38 performs the correction of the X-ray myocardium perfusion image and the CT myocardium perfusion image by distinguishing cases, namely, a case of displaying the both images as an image having a thickness component, and a case of displaying the both images as an image not having thickness component, i.e., an image with a unit thickness. It is assumed that when the X-ray diagnosis apparatus 300 starts to take an X-ray projection image, the operator preliminarily specifies in which of the cases the X-ray myocardium perfusion image and the CT myocardium perfusion image are to be displayed as an image.

Specifically, when displaying each of an X-ray myocardium perfusion image and a CT myocardium perfusion image as an image having a thickness component, the image correction unit 38 does not perform correction of the X-ray myocardium perfusion image, but performs only correction of the CT myocardium perfusion image. In such case, the image correction unit 38 creates a CT myocardium perfusion image having a thickness component by performing processing of conversion into two dimension of integrating perfusion values only in the myocardium region, on the CT myocardium perfusion image that is a three-dimensional image.

At first, the image correction unit 38 acquires information indicating an imaging direction at a moment when the X-ray projection image is taken, from supplementary information given to the X-ray myocardium perfusion image created by the X-ray perfusion-image creating unit 10. For example, as the information indicating the imaging direction, the image correction unit 38 acquires information indicating a state of a mechanism at the moment of radiographing with X-ray by the X-ray diagnosis apparatus 300 that takes the X-ray projection image. The state of a mechanism here means, for example, the angle of the C-arm 4, and the position of the couch on which the subject is placed.

The image correction unit 38 then extracts information indicating the thickness of the myocardium along the imaging direction as thickness information. Moreover, the image correction unit 38 corrects the thickness of the myocardium in the CT myocardium perfusion image based on the extracted thickness information. When correcting, the image correction unit 38 converts the CT myocardium perfusion image into two dimension by integrating the thickness components of the myocardium in the CT myocardium perfusion image.

FIG. 7 is a schematic diagram that depicts an example of correction of a CT myocardium perfusion image by the image correction unit 38. Suppose, for example, as shown in FIG. 7, a CT myocardium perfusion image C of a myocardium has been created. Moreover, as shown in FIG. 7, assuming that paths of X-ray are obtained from the imaging direction at the moment of taking an X-ray projection image, a path passes through a path $X_1$ of X-ray near an end of the myocardium, and another path passes through a path $X_2$ near the center of the myocardium. In such case, the image correction unit 38 integrates pixel values $P_1$ of pixels on the path $X_1$ inside the myocardium in the CT myocardium perfusion image C. Moreover, the image correction unit 38 integrates pixel values $P_2$ in a lower inside of the myocardium among pixels on the path $X_2$ inside the myocardium. The image correction unit 38 performs the processing of conversion into two dimension on all of the paths of X-ray passing through the myocardium. As a result, a CT myocardium perfusion image F that is converted into two dimension is created.

By contrast, when displaying each of an X-ray myocardium perfusion image and a CT myocardium perfusion image as an image not having thickness component, the image correction unit 38 performs only correction of the X-ray myocardium perfusion image. In such case, for example, the image correction unit 38 acquires the thickness of each part of the myocardium from the myocardium region information extracted by the CT perfusion-image creating unit 11, proportionally divides pixel values of pixels included in the X-ray myocardium perfusion image by the acquired thickness, thereby correcting the X-ray myocardium perfusion image.

FIG. 8 is a schematic diagram for explaining correction of thickness components by the image correction unit 38. Suppose, for example, as shown in FIG. 8, as a path of X-ray that passes through a myocardium M, the path $X_1$ reaching a detecting element $D_1$ of the X-ray detecting unit 2 from the X-ray generating unit 1, and the path $X_2$ reaching a detecting element $D_2$ of the X-ray detecting unit 2 from the X-ray generating unit 1 are present. Moreover, suppose that an integrated quantity of photons detected by the detecting element $D_i$ is $F_1$, and an integrated quantity of photons detected by the detecting element $D_2$ is $F_2$.

For example, the image correction unit 38 acquires respective thicknesses of parts through which the path $X_1$ and the path $X_2$ pass in the myocardium M, from the myocardium region information extracted by the CT perfusion-image creating unit 11. As a result, for example, as shown in FIG. 8, suppose that the thickness of a part through which the path $X_1$ passes is $d_1$. Furthermore, suppose that the thickness of a part through which the path $X_2$ passes on the side of the X-ray generating unit 1 is $d_2$, and the thickness of a part through which the path $X_2$ passes on the side of the X-ray detecting unit 2 is $d_3$.

In such case, for example, the image correction unit 38 corrects thickness components in the X-ray myocardium perfusion image, by multiplying the pixel value of a pixel corresponding to the detecting element $D_1$ in the X-ray myocardium perfusion image by $F_1/d_i$, and multiplying the pixel value of a pixel corresponding to the detecting element $D_2$ by $F_2/(d_2+d_3)$.

A flow of image display by the X-ray diagnosis apparatus 300 according to the third embodiment is explained below. FIG. 9 is a flowchart of a flow of image display by the X-ray diagnosis apparatus 300 according to the third embodiment.

As shown in FIG. 9, according to the third embodiment, after a CT image is taken by the X-ray CT apparatus 200 (Yes at Step S301); the CT-data acquiring unit 9 acquires the CT image taken by the X-ray CT apparatus 200 (Step S302).

Subsequently, the CT perfusion-image creating unit 11 extracts myocardium region information from the CT image acquired by the CT-data acquiring unit 9 (Step S303). Moreover, the CT perfusion-image creating unit 11 creates at least one kind of CT myocardium perfusion image from the acquired CT image (Step S304).

On the other hand, when the operation unit 6 receives an instruction to start X-ray radiography from the operator (Yes at Step S305); the X-ray data acquiring unit 8 acquires an X-ray projection image created by the X-ray detecting unit 2 (Step S306). Subsequently, the X-ray perfusion-image creating unit 10 creates an X-ray myocardium perfusion image of a certain kind from the X-ray projection image acquired by the X-ray data acquiring unit 8 (Step S307).

When the X-ray myocardium perfusion image is created by the X-ray perfusion-image creating unit 10, the image selecting unit 13 determines whether there is a CT myocardium perfusion image of the same kind as the created X-ray myocardium perfusion image, among the CT myocardium perfusion images created by the CT perfusion-image creating unit 11 (Step S308).

If there is no CT myocardium perfusion image of the same kind as the X-ray myocardium perfusion image (No at Step S308); the image selecting unit 13 instructs the CT perfusion-image creating unit 11 to create a CT myocardium perfusion image of the same kind as the X-ray myocardium perfusion image (going back to Step S304). By contrast, if a CT myocardium perfusion image of the same kind as the X-ray myocardium perfusion image is obtained (Yes at Step S308); the image selecting unit 13 selects the obtained CT myocardium perfusion image (Step S309).

Subsequently, the image correction unit 38 performs the processing of conversion into two dimension on the CT myocardium perfusion image selected by the image selecting unit 13 (Step S310).

At that moment, if it is instructed from the operator so as to display the X-ray myocardium perfusion image and the CT myocardium perfusion image as images that do not include thickness component (No at Step S311), the image correction unit 38 corrects thickness components of the X-ray myocardium perfusion image based on the myocardium region information extracted by the CT perfusion-image creating unit 11 (Step S312).

The display control unit 34 then causes the display unit 7 to display the X-ray projection image acquired by the X-ray data acquiring unit 8, the X-ray myocardium perfusion image created by the X-ray perfusion-image creating unit 10, and the CT myocardium perfusion image corrected by the image correction unit 38 in parallel (Step S313).

By contrast, if it is instructed from the operator so as to display the X-ray myocardium perfusion image and the CT myocardium perfusion image as images that include thickness components (Yes at Step S311), the display control unit 34 causes the display unit 7 to display the X-ray projection image acquired by the X-ray data acquiring unit 8, the X-ray myocardium perfusion image created by the X-ray perfusion-image creating unit 10, and the CT myocardium perfusion image converted into two dimension by the image correction unit 38 in parallel (Step S313).

As described above, according to the third embodiment, the CT perfusion-image creating unit 11 creates a CT myocardium perfusion image, and extracts myocardium region information from a CT image taken by the X-ray CT apparatus 200. The image correction unit 38 then corrects either an X-ray myocardium perfusion image or the CT myocardium perfusion image, so as to match thickness components of a myocardium included in the X-ray myocardium perfusion image and the CT myocardium perfusion image, based on the myocardium region information extracted by the CT perfusion-image creating unit 11.

Therefore, according to the third embodiment, there is no necessity of considering thickness component of the myocardium, an X-ray myocardium perfusion image and a CT myocardium perfusion image can be compared further easily.

According to the third embodiment, it is configured that the image correction unit 38 creates a CT myocardium perfusion image having a thickness component by performing processing of conversion into two dimension of integrating perfusion values only in a myocardium region, on a CT myocardium perfusion image that is a three-dimensional image. For example, the CT myocardium perfusion image can be displayed alone.

In such case, specifically, the CT perfusion-image creating unit 11 creates a CT myocardium perfusion image so as to indicate blood flow dynamics in the myocardium from a CT image taken by the X-ray CT apparatus 200. In addition, the image correction unit 38 extracts a region occupied by the myocardium from the CT myocardium perfusion image created by the CT perfusion-image creating unit 11, and performs processing of conversion into two dimension of integrating perfusion values only in the extracted region, thereby creating a projection image of the myocardium. The display control unit 34 then causes the display unit 7 to display the projection image created by the image correction unit 38.

In this way, the perfusion values of the CT myocardium perfusion image that is a three-dimensional perfusion image are composited and converted into a two-dimensional image, accordingly, when observing the X-ray myocardium perfusion image that is a two-dimensional image and the CT myocardium perfusion image in comparison with each other, an abnormal portion in the organ can be easily found.

The first to third embodiments are explained above; however, the present invention can be implemented by various different embodiments in addition to the embodiments described above.

For example, it can be configured such that when an ischemic region is detected in a myocardium through a diagnosis by an X-ray CT apparatus, the detected ischemic region is to be displayed in a highlighted manner on an X-ray myocardium perfusion image.

In such case, for example, in addition to a CT image, the CT-data acquiring unit 9 further acquires region-of-interest information indicating a region of interest that is set as the ischemic region on the CT image by the operator.

When the display control unit 14 causes the display unit 7 to display an X-ray myocardium perfusion image and a CT myocardium perfusion image, the display control unit 14 causes the display unit 7 to display an area on the X-ray myocardium perfusion image corresponding to the region of interest set on the CT image in a highlighted manner, based on the region-of-interest information acquired by the CT-data acquiring unit 9.

FIG. 10 is a schematic diagram that depicts an example when displaying an ischemic region in a highlighted manner on an X-ray myocardium perfusion image. As shown in FIG. 10, for example, the display control unit 14 causes display of an animation R indicating an area of the ischemic region on each of the X-ray myocardium perfusion image displayed by the monitor 7b, and the CT myocardium perfusion image displayed by the monitor 7c. Accordingly, a doctor can easily find a region that the doctor needs to observe particularly carefully.

Moreover, it can be configured such that when an ischemic region is detected in a myocardium through a diagnosis by the X-ray CT apparatus, imaging conditions for radiographing by the X-ray diagnosis apparatus are controlled such that the detected ischemic region is to be easily observed.

In such case, for example, in addition to a CT image, the CT-data acquiring unit 9 further acquires region-of-interest information indicating a region of interest that is set as the ischemic region on the CT image by the operator. The C-arm control unit 15 then turns the C-arm 4 such that the region of interest is to be radiographed from the front side or a lateral side, based on region-of-interest information acquired by the CT-data acquiring unit 9. Specifically, the C-arm control unit 15 calculates a radiation angle of X-ray at which the region of interest is radiographed from the front side or a lateral side, and turns the C-arm 4 by driving the C-arm rotating/moving mechanism 5 so as to radiate an X-ray at the calculated radiation angle onto the subject P.

When the C-arm 4 is turned so as to radiograph a region of interest from the front side, an ischemic region is rendered to the widest in an X-ray myocardium perfusion image, so that a perfusion state in the ischemic region can be easily observed. Moreover, because an X-ray is vertically radiated onto the ischemic region, thickness component of the myocardium does not need to be taken into account when observing the perfusion state.

Furthermore, when the C-arm 4 is turned so as to radiograph a region of interest from a lateral side, the ischemic region is rendered along the imaging direction, so that a state of wall movement in the ischemic region is indicated most clearly. Accordingly, to what extent the amount of movement of the myocardium decreases in the ischemic region can be easily grasped. For example, wall movement in the ischemic region is diagnosed by observing an X-ray myocardium perfusion image obtained by radiographing a left ventricle with a contrast agent after the C-arm control unit 15 turns the C-arm 4.

The above embodiments are explained in cases where an X-ray projection image created by the X-ray diagnosis apparatus 100 is a two-dimensional image. However, recently, a technology of taking a three-dimensional image by an X-ray diagnosis apparatus is developed. Therefore, each of the embodiments explained above can be configured to create an X-ray myocardium perfusion image of a three-dimensional image by using a three-dimensional image instead of a two-dimensional image.

Moreover, the above embodiments are explained in cases of using a CT myocardium perfusion image created from a CT image taken by an X-ray CT apparatus; however, the present invention is not limited to this. For example, the embodiments can be similarly applied to a case of using a perfusion image created from an image taken by another diagnostic imaging apparatus, such as an MRI apparatus or a PET apparatus.

Furthermore, the third embodiment is explained above in a case of correcting thickness components of a myocardium included in an X-ray myocardium perfusion image or a CT myocardium perfusion image; however, it can be configured to correct, for example, the thickness of a blood vessel. FIG. 11 is a flowchart of a flow of image display by the X-ray diagnosis apparatus 300 according to the third embodiment.

As shown in FIG. 11, according to the third embodiment, after a CT image is taken by the X-ray CT apparatus 200 (Yes at Step S401); the CT-data acquiring unit 9 acquires the CT image taken by the X-ray CT apparatus 200 (Step S402). Subsequently, the CT perfusion-image creating unit 11 creates a CT myocardium perfusion image from the CT image acquired by the CT-data acquiring unit 9 (Step S403).

Furthermore, the CT perfusion-image creating unit 11 extracts a region including a blood vessel as a blood-vessel region from the CT image (Step S404). At that moment, for example, the CT perfusion-image creating unit 11 receives from the operator an operation specifying an area including a blood vessel on the CT myocardium perfusion image, and extracts the area specified by the operator as the blood-vessel region. Alternatively, the CT perfusion-image creating unit 11 automatically extracts a blood-vessel region from the CT myocardium perfusion image by using, for example, known region-extracting processing. Alternatively, the CT perfusion-image creating unit 11 stores information indicating an area including a certain blood vessel included in the heart, and extracts a blood-vessel region based on the stored information. The area indicated by the information is determined based on, for example, an anatomical point of view.

On the other hand, when the operation unit 6 receives an instruction to start X-ray radiography from the operator (Yes at Step S405); the X-ray data acquiring unit 8 acquires an X-ray projection image created by the X-ray detecting unit 2 (Step S406). Subsequently, the X-ray perfusion-image creating unit 10 creates an X-ray myocardium perfusion image from the X-ray projection image acquired by the X-ray data acquiring unit 8 (Step S407).

When the X-ray myocardium perfusion image is created by the X-ray perfusion-image creating unit 10, the image correction unit 38 acquires information indicating an imaging direction at the moment when the X-ray projection image is taken, from supplementary information given to the created X-ray myocardium perfusion image (Step S408). At that moment, for example, the image correction unit 38 acquires information indicating a state of a mechanism at the moment of radiographing with X-ray by the X-ray diagnosis apparatus 300 that takes the X-ray projection image, as information indicating the imaging direction. The state of a mechanism here means, for example, the angle of the C-arm 4, and the position of the couch on which the subject is placed.

After the X-ray myocardium perfusion image is created by the X-ray perfusion-image creating unit 10, the image correction unit 38 performs the processing of conversion into two dimension on the CT myocardium perfusion image created by the CT perfusion-image creating unit 11 (Step S409). Furthermore, the image correction unit 38 calculates the thickness of the blood vessel along the imaging direction in the blood-vessel region extracted by the CT perfusion-image creating unit 11, based on the acquired information indicating the imaging direction (Step S410).

Figure 12A:
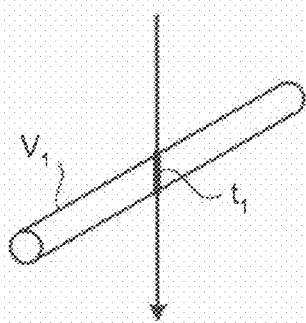
FIGS. 12A to 12D are schematic diagrams for explaining calculation of a thickness of a blood vessel by the image correction unit.
Figure 12B:
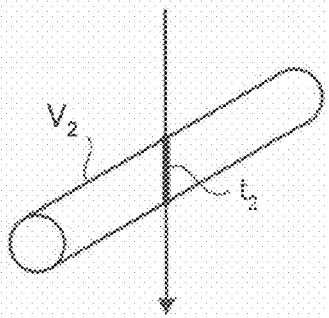
Figure 12C:
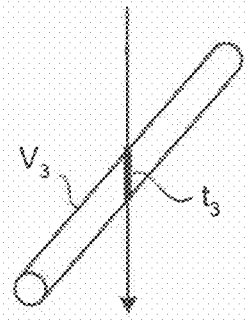
Figure 12D:
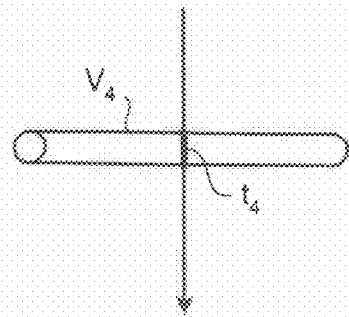

FIGS. 12A to 12D are schematic diagrams for explaining calculation of the thickness of a blood vessel by the image correction unit 38. Arrows shown in FIGS. 12A to 12D represent the imaging direction at the moment of radiographing with X-ray. As shown in FIGS. 12A and 12B, for example, when a blood vessel $V_1$ and a blood vessel $V_2$ thicker than the blood vessel $V_1$ are radiographed with X-ray from the same imaging direction, a thickness $t_2$ of the blood vessel $V_2$ is larger than a thickness $t_1$ of the blood vessel $V_1$, in terms of the thickness along the imaging direction. Moreover, as shown in FIGS. 12C and 12D, even when blood vessels $V_3$ and $V_4$ of the same thickness are radiographed from the same imaging direction, a thickness $t_3$ of the blood vessel $V_3$ and a thickness $t_4$ of the blood vessel $V_4$ along the imaging direction are different in size, depending on an angle of each blood vessel at a moment of radiographing. Therefore, with respect to a blood vessel included in a blood-vessel region extracted by the CT perfusion-image creating unit 11, the image correction unit 38 calculates the thickness of the blood vessel based on the angle of the blood vessel, the size and the direction of the blood vessel.

Returning to explanation of FIG. 11, after calculating the thickness of the blood vessel, the image correction unit 38 creates an X-ray myocardium perfusion image in which the thickness of a blood vessel is corrected, based on the calculated thickness of the blood vessel (Step S411). At that moment, for example, the image correction unit 38 divides pixel values with respect to each pixel of a blood-vessel part included in the X-ray myocardium perfusion image in accordance with the thickness of the blood vessel, thereby creating the X-ray myocardium perfusion image in which the thickness of the blood vessel is corrected.

The display control unit 34 then causes the display unit 7 to display the X-ray myocardium perfusion image in which the thickness of the blood vessel is corrected by the image correction unit 38, and the CT myocardium perfusion image created by the CT perfusion-image creating unit 11 in parallel (Step S412).

In this way, for example, the X-ray perfusion-image creating unit 10 creates an X-ray myocardium perfusion image indicating blood flow dynamics in a myocardium from an X-ray projection image of a subject given with a contrast agent. The CT perfusion-image creating unit 11 extracts a region including a blood vessel as a blood-vessel region from a CT image taken by the X-ray CT apparatus 200. The image correction unit 38 calculates the thickness of the blood vessel in the blood-vessel region, and creates an X-ray myocardium perfusion image in which the thickness of the blood vessel is corrected based on the calculated thickness of the blood vessel. The display control unit 34 then causes the display unit 7 to display the X-ray myocardium perfusion image in which the thickness of the blood vessel is corrected. Accordingly, because the thickness of a blood vessel does not need to be taken into account when reading an image, an X-ray myocardium perfusion image and a CT myocardium perfusion image can be more easily compared.

Explained above is a case where the thickness of a blood vessel included in an X-ray myocardium perfusion image is corrected by using a CT image taken by the X-ray CT apparatus 200. However, recently, a technology of creating a three-dimensional blood-vessel image by an X-ray diagnosis apparatus is proposed (for example, see U.S. Pat. No. 6,501,848, or U.S. Pat. No. 6,047,080). Therefore, for example, a three-dimensional blood-vessel image created by an X-ray diagnosis apparatus can be used instead of a CT image.

Generally, when a heart is radiographed by an X-ray diagnosis apparatus, a contrast agent is injected into an artery of a subject. In such case, among a left anterior descending artery, a left circumflex, and a right coronary artery, which are main coronary arteries nourishing a myocardium, one or two of the three are simultaneously contrasted. By contrast, generally, when a heart is radiographed by an X-ray CT apparatus, a contrast agent is injected into a vein of a subject. In such case, a left anterior descending artery, a left circumflex, and a right coronary artery are three simultaneously contrasted.

In this way, an X-ray myocardium perfusion image and a CT myocardium perfusion image are different in the number of coronary arteries to be contrasted, consequently, each of the images cannot be easily compared when comparing a myocardium region dominated by coronary arteries. Therefore, for example, the X-ray myocardium perfusion image and/or the CT myocardium perfusion image can be corrected such that the contrasted blood vessel and its dominant region match up.

FIGS. 13 and 14 are schematic diagrams that depict an example when correcting a myocardium perfusion image so as to match contrasted blood vessels with each other. Suppose, for example, as shown in FIG. 13, a CT myocardium perfusion image $CT_1$ in which a left anterior descending artery LAD, a left circumflex LCX, and a right coronary artery RCA are each contrasted has been created. Moreover, suppose that an X-ray myocardium perfusion image $XR_1$ in which only the left anterior descending artery LAD and the left circumflex LCX are contrasted has bee created.

In such case, for example, the image correction unit corrects the CT myocardium perfusion image $CT_1$ such that the same coronary arteries as contrasted on the X-ray myocardium perfusion image $XR_1$ is to be contrasted. For example, as shown in FIG. 13, the image correction unit extracts a coronary artery from a region of interest S set on the CT myocardium perfusion image $CT_1$. The region of interest here is arbitrarily set by, for example, an operator. Alternatively, the region of interest can be set in advance so as to include a certain coronary artery based on an anatomical point of view. Subsequently, the image correction unit creates a CT myocardium perfusion image $CT_2$ into which the coronary arteries included in the region of interest and a myocardium region dominated by the coronary arteries are extracted. After that, the image correction unit performs the processing of conversion into two dimension on the CT myocardium perfusion image $CT_2$, thereby creating a CT myocardium perfusion image $CT_3$ converted into two dimension.

For example, as shown in FIG. 13, when a region of interest is set so as to include the left anterior descending artery LAD and the left circumflex LCX, the CT myocardium perfusion image $CT_3$ becomes an image in which the left anterior descending artery LAD and the left circumflex LCX and their dominant region are contrasted. Accordingly, the CT myocardium perfusion image $CT_3$ is obtained, in which the same coronary arteries as contrasted on the X-ray myocardium perfusion image $XR_1$ and their dominant region are contrasted. Accordingly, when diagnosing coronary arteries and their dominant region of a heart, the X-ray myocardium perfusion image $XR_1$ and the CT myocardium perfusion image $CT_3$ can be easily compared.

Suppose, for example, as shown in FIG. 14, a CT myocardium perfusion image $CT_4$ in which the left anterior descending artery LAD, the left circumflex LCX, and the right coronary artery RCA are each contrasted has been created. Moreover, suppose that an X-ray myocardium perfusion image $XR_2$ in which only the left anterior descending artery LAD and the left circumflex LCX are contrasted, and an X-ray myocardium perfusion image $XR_3$ in which only the right coronary artery RCA is contrasted have been created.

In such case, for example, the image correction unit 38 corrects the X-ray myocardium perfusion images $XR_2$ and $XR_3$ such that the same coronary arteries as contrasted on a CT myocardium perfusion image $CT_4$ are to be contrasted. For example, as shown in FIG. 13, the image correction unit performs the processing of conversion into two dimension on the CT myocardium perfusion image $CT_4$, thereby creating a CT myocardium perfusion image CF converted into two dimension. The CT myocardium perfusion image CF is an image on which the left anterior descending artery LAD, the left circumflex LCX, and the right coronary artery RCA are each contrasted.

Moreover, the image correction unit 38 creates an X-ray myocardium perfusion image XF in which the left anterior descending artery LAD, the left circumflex LCX, and the right coronary artery RCA are each contrasted by combining the X-ray myocardium perfusion image $XR_2$ and the X-ray myocardium perfusion image $XR_3$. Accordingly, the X-ray myocardium perfusion image XF is obtained, in which the same coronary arteries as contrasted on the CT myocardium perfusion image CF and their dominant region are contrasted. Accordingly, when diagnosing coronary arteries and their dominant region of a heart, the X-ray myocardium perfusion image XF and the CT myocardium perfusion image CF can be easily compared.

The embodiment described above is explained in a case of correcting pixel values of pixels included in a perfusion image, based on the thickness of a myocardium or the thickness of a blood vessel. For example, there is a case of using a value indicating a correlation between the TDC in the blood-vessel region and the TDC in the myocardium region, as an index value indicating blood flow dynamics in a perfusion image (for example, JP-A 2008-136800 (KOKAI)). In such case, for example, the value of TDC in the blood-vessel region is corrected based on the thickness of the blood vessel; the value of TDC in the myocardium region is corrected based on the thickness of the myocardium; and the index value can be calculated by using each of the corrected values.

As described above, the image display apparatus and the X-ray diagnosis apparatus according to the embodiments of the present invention are useful when comparing a plurality of kinds of perfusion images, and particularly suitable when comparing perfusion images during a treatment using an X-ray diagnosis apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus, comprising:
   an X-ray perfusion-image creating unit that creates an X-ray perfusion image indicating blood flow dynamics in a certain organ from an X-ray projection image of a subject injected with a contrast agent;
   a thickness-information extracting unit that extracts thickness information indicating a thickness of tissue of the organ from a three-dimensional image taken by a diagnostic imaging apparatus;
   a correction-image creating unit that creates a corrected perfusion image by proportionally dividing pixel values of the tissue of the organ in the X-ray perfusion image by the thickness indicated by the thickness information; and
   a display that displays the corrected perfusion image.

2. The image display apparatus according to claim 1, further comprising a diagnosis perfusion-image creating unit that creates a diagnosis perfusion image indicating blood flow dynamics in the organ from the three-dimensional image taken by the diagnostic imaging apparatus, wherein the display displays the corrected perfusion image and the diagnosis perfusion image.

3. The image display apparatus according to claim 2, wherein
  the organ is a heart, and
  the correction-image creating unit further corrects the corrected perfusion image such that a same blood vessel as a blood vessel contrasted on the diagnosis perfusion image is to be contrasted.

4. The image display apparatus according to claim 1, wherein the thickness-information extracting unit acquires information indicating an imaging direction at a moment when the X-ray projection image is taken, and extracts information indicating a thickness of the tissue of the organ along the imaging direction as the thickness information.

5. The image display apparatus according to claim 4, wherein the thickness-information extracting unit acquires information indicating a state of a mechanism at a moment of radiographing with X-rays by an X-ray radiographic apparatus that takes the X-ray projection image, as information indicating the imaging direction.

6. The image display apparatus according to claim 1, wherein the display further displays a ischemic region on the corrected perfusion image.

7. The image display apparatus according to claim 1, wherein the diagnostic imaging apparatus is one of an X-ray Computed Tomography apparatus, a Magnetic Resonance Imaging apparatus, and a Positron Emission Tomography apparatus.

8. An image display apparatus, comprising:
  a diagnosis perfusion-image creating unit that creates a diagnosis perfusion image indicating blood flow dynamics in a certain organ from a three-dimensional image taken by a diagnostic imaging apparatus;
  a thickness-information extracting unit that extracts thickness information indicating a thickness of tissue of the organ from the three-dimensional image;
  a correction-image creating unit that creates a corrected perfusion image by integrating pixel values of the tissue of the organ corresponding to the thickness indicated by the thickness information in the diagnosis perfusion image so as to convert the diagnosis perfusion image into a two-dimensional image; and
  a display that displays the corrected perfusion image.

9. The image display apparatus according to claim 8, further comprising an X-ray perfusion-image creating unit that creates an X-ray perfusion image indicating blood flow dynamics in the organ from an X-ray projection image of a subject injected with a contrast agent, wherein the display displays the corrected perfusion image and the X-ray perfusion image.

10. The image display apparatus according to claim 9, wherein
  the organ is a heart, and
  the correction-image creating unit further corrects the corrected perfusion image such that a same blood vessel as a blood vessel contrasted on the X-ray perfusion image is to be contrasted.

11. The image display apparatus according to claim 8, wherein the thickness-information extracting unit acquires information indicating an imaging direction at a moment when the X-ray projection image is taken, and extracts information indicating a thickness of the tissue of the organ along the imaging direction as the thickness information.

12. The image display apparatus according to claim 11, wherein the thickness-information extracting unit acquires information indicating a state of a mechanism at a moment of radiographing with X-rays by an X-ray radiographic apparatus that takes the X-ray projection image, as information indicating the imaging direction.

13. The image display apparatus according to claim 8, wherein the display further displays a ischemic region on the corrected perfusion image.

14. The image display apparatus according to claim 8, wherein the diagnostic imaging apparatus is one of an X-ray Computed Tomography apparatus, a Magnetic Resonance Imaging apparatus, and a Positron Emission Tomography apparatus.

15. An image display apparatus, comprising:
  an X-ray perfusion-image creating unit that creates an X-ray perfusion image indicating blood flow dynamics in a certain organ from an X-ray projection image of a subject injected with a contrast agent;
  a blood-vessel region extracting unit that extracts a region including a blood vessel as a blood vessel region from a three-dimensional image taken by a diagnostic imaging apparatus;
  a blood-vessel thickness calculating unit that calculates a thickness of the blood vessel in the blood vessel region;
  a correction-image creating unit that creates a blood-vessel corrected perfusion image by proportionally dividing pixel values of the blood vessel in the X-ray perfusion image by the thickness of the blood vessel calculated by the blood-vessel thickness calculating unit; and
  a display that displays the blood-vessel corrected perfusion image.

16. The image display apparatus according to claim 15, further comprising a diagnosis perfusion-image creating unit that creates a diagnosis perfusion image indicating blood flow dynamics in the organ from the three-dimensional image taken by the diagnostic imaging apparatus, wherein the display displays the blood-vessel corrected perfusion image and the diagnosis perfusion image.

17. The image display apparatus according to claim 16, wherein
  the organ is a heart, and
  the correction-image creating unit further corrects the blood-vessel corrected perfusion image such that a same blood vessel as a blood vessel contrasted on the diagnosis perfusion image is to be contrasted.

18. The image display apparatus according to claim 15, wherein the blood-vessel thickness calculating unit acquires information indicating an imaging direction at a moment when the X-ray projection image is taken, and calculates a thickness of the blood vessel along the imaging direction.

19. The image display apparatus according to claim 18, wherein the blood-vessel thickness calculating unit acquires information indicating a state of a mechanism at a moment of radiographing with X-rays by an X-ray radiographic apparatus that takes the X-ray projection image, as information indicating the imaging direction.

20. The image display apparatus according to claim 15, wherein the display further displays a ischemic region on the blood-vessel corrected perfusion image.

21. The image display apparatus according to claim 15, wherein the diagnostic imaging apparatus is one of an X-ray Computed Tomography apparatus, a Magnetic Resonance Imaging apparatus, and a Positron Emission Tomography apparatus.

22. An X-ray diagnosis apparatus, comprising:
  an X-ray generating unit that generates an X-ray;
  an X-ray image creating unit that creates an X-ray projection image by detecting X-rays passing through a subject injected with a contrast agent;

an X-ray perfusion-image creating unit that creates an X-ray perfusion image indicating blood flow dynamics in a certain organ from the X-ray projection image;

a thickness-information extracting unit that extracts thickness information indicating a thickness of tissue of the organ from a three-dimensional image taken by a diagnostic imaging apparatus;

a correction-image creating unit that creates a corrected perfusion image by proportionally dividing pixel values of the tissue of the organ in the X-ray perfusion image by the thickness indicated by the thickness information; and a display that displays the corrected perfusion image.

23. The X-ray diagnosis apparatus according to claim 22, wherein the display further displays a ischemic region on the corrected perfusion image.

24. The X-ray diagnosis apparatus according to claim 22, wherein the diagnostic imaging apparatus is one of an X-ray Computed Tomography apparatus, a Magnetic Resonance Imaging apparatus, and a Positron Emission Tomography apparatus.

25. An X-ray diagnosis apparatus, comprising:
an X-ray generating unit that generates an X-ray;
an X-ray image creating unit that creates an X-ray projection image by detecting X-rays passing through a subject injected with a contrast agent;
a diagnosis perfusion-image creating unit that creates a diagnosis perfusion image indicating blood flow dynamics in a certain organ from a three-dimensional image taken by a diagnostic imaging apparatus;
a thickness-information extracting unit that extracts thickness information indicating a thickness of tissue of the organ from the three-dimensional image;
a correction-image creating unit that creates a corrected perfusion image by integrating pixel values of the tissue of the organ corresponding to the thickness indicated by the thickness information in the diagnosis perfusion image so as to convert the diagnosis perfusion image into a two-dimensional image; and
a display that displays the X-ray projection image and the corrected perfusion image.

26. The X-ray diagnosis apparatus according to claim 25, wherein the display further displays a ischemic region on the corrected perfusion image.

27. The X-ray diagnosis apparatus according to claim 25, wherein the diagnostic imaging apparatus is one of an X-ray Computed Tomography apparatus, a Magnetic Resonance Imaging apparatus, and a Positron Emission Tomography apparatus.

28. An X-ray diagnosis apparatus, comprising:
an X-ray generating unit that generates an X-ray;
an X-ray image creating unit that creates an X-ray projection image by detecting X-rays passing through a subject injected with a contrast agent;
an X-ray perfusion-image creating unit that creates an X-ray perfusion image indicating blood flow dynamics in a certain organ from the X-ray projection image;
a blood-vessel region extracting unit that extracts a region including a blood vessel as a blood vessel region from a three-dimensional image taken by a diagnostic imaging apparatus;
a blood-vessel thickness calculating unit that calculates a thickness of the blood vessel in the blood vessel region;
a correction-image creating unit that creates a blood-vessel corrected perfusion image by proportionally dividing pixel values of the blood vessel in the X-ray perfusion image by the thickness of the blood vessel calculated by the blood-vessel thickness calculating unit; and
a display that displays the blood-vessel corrected perfusion image.

29. The X-ray diagnosis apparatus according to claim 28, wherein the display further displays a ischemic region on the blood-vessel corrected perfusion image.

30. The X-ray diagnosis apparatus according to claim 28, wherein the diagnostic imaging apparatus is one of an X-ray Computed Tomography apparatus, a Magnetic Resonance Imaging apparatus, and a Positron Emission Tomography apparatus.

* * * * *